US012213637B2

(12) United States Patent
Safavi

(10) Patent No.: US 12,213,637 B2
(45) Date of Patent: Feb. 4, 2025

(54) PIPETTE TIP WASHING DEVICE

(71) Applicant: GRENOVA, INC., Richmond, VA (US)

(72) Inventor: Ali Safavi, Richmond, VA (US)

(73) Assignee: GRENOVA, INC., Richmond, VA (US)

( * ) Notice: Subject to any disclaimer, the term of this patent is extended or adjusted under 35 U.S.C. 154(b) by 0 days.

(21) Appl. No.: 18/454,661

(22) Filed: Aug. 23, 2023

(65) Prior Publication Data

US 2023/0389771 A1 Dec. 7, 2023

Related U.S. Application Data

(60) Continuation of application No. 16/821,710, filed on Mar. 17, 2020, now Pat. No. 11,737,641, which is a
(Continued)

(51) Int. Cl.
*A47L 15/42* (2006.01)
*A61L 2/10* (2006.01)
*B01L 3/02* (2006.01)
*B01L 9/00* (2006.01)
*B08B 3/02* (2006.01)
(Continued)

(52) U.S. Cl.
CPC ............ *A47L 15/4242* (2013.01); *A61L 2/10* (2013.01); *B01L 3/0275* (2013.01); *B01L 9/543* (2013.01); *B01L 13/02* (2019.08); *B08B 3/02* (2013.01); *B08B 7/0057* (2013.01); *B08B 9/00* (2013.01); *G01N 35/1004* (2013.01); *B01L 2400/0487* (2013.01); *B01L 2400/0605* (2013.01)

(58) Field of Classification Search
CPC ...... A47L 15/4242; A61L 2/10; B01L 3/0275; B01L 9/543; B01L 13/02; B01L 2400/0487; B01L 2400/0605; B08B 3/02; B08B 7/0057; B08B 9/00; G01N 35/1004
See application file for complete search history.

(56) References Cited

U.S. PATENT DOCUMENTS 2,548,363 A 4/1951 Gray
4,566,203 A 1/1986 Johnson
(Continued)

FOREIGN PATENT DOCUMENTS

EP 0 919 282 A1 6/1999

OTHER PUBLICATIONS

International Search Report and Written Opinion for Application No. PCT/US2016/032634, dated Aug. 19, 2016.
(Continued)

*Primary Examiner* — Alexander Markoff
(74) *Attorney, Agent, or Firm* — Welsh Flaxman & Gitler LLC

(57) ABSTRACT

A washing device comprises a manifold dispenser comprising at least one liquid input and a plurality of liquid outputs that operably direct fluid to contact a plurality of laboratory consumables held by a rack in the washing device. A number of the plurality of liquid outputs being at least equal to a number of the plurality of laboratory consumables such that each liquid output of the plurality of liquid outputs operably directs the liquid at a corresponding laboratory consumable of the plurality of laboratory consumables.

5 Claims, 35 Drawing Sheets

Related U.S. Application Data continuation of application No. 16/361,059, filed on Mar. 21, 2019, now Pat. No. 10,631,707, which is a division of application No. 15/042,578, filed on Feb. 12, 2016, now Pat. No. 10,285,564, which is a continuation-in-part of application No. 14/796,712, filed on Jul. 10, 2015, now Pat. No. 9,744,570, which is a continuation-in-part of application No. 14/266,330, filed on Apr. 30, 2014, now Pat. No. 9,421,289.

(60) Provisional application No. 61/890,523, filed on Oct. 14, 2013, provisional application No. 61/817,715, filed on Apr. 30, 2013.

(51) Int. Cl.
  *B08B 7/00* (2006.01)
  *B08B 9/00* (2006.01)
  *G01N 35/10* (2006.01)

(56) References Cited

U.S. PATENT DOCUMENTS

| | | | |
|---|---|---|---|
| 4,753,681 A | 6/1988 | Giuffrida et al. | |
| 5,325,609 A | 7/1994 | Wells | |
| 5,525,302 A * | 6/1996 | Astle | B01L 3/0279 422/522 |
| 6,724,608 B2 | 4/2004 | Hensley et al. | |
| 7,017,594 B2 | 3/2006 | Kurunczi et al. | |
| 7,067,046 B2 | 6/2006 | Schroeder | |
| 7,094,314 B2 | 8/2006 | Kurunczi | |
| 7,270,730 B2 | 9/2007 | Schroeder | |
| 7,300,525 B2 | 11/2007 | Furst et al. | |
| 7,367,344 B2 | 5/2008 | Kurunczi et al. | |
| 8,021,611 B2 | 9/2011 | Roach et al. | |
| 8,118,042 B2 | 2/2012 | Ngo | |
| 8,367,022 B2 | 2/2013 | Warhurst | |
| 8,372,356 B2 | 2/2013 | Warhurst | |
| 9,421,289 B2 * | 8/2016 | Safavi | A47L 15/0084 |
| 9,579,696 B2 * | 2/2017 | Safavi | B01L 13/02 |
| 9,744,570 B2 | 8/2017 | Safavi | |
| 10,155,055 B2 * | 12/2018 | Safavi | B08B 3/08 |
| 10,285,564 B2 * | 5/2019 | Safavi | B08B 7/0057 |
| 11,737,641 B2 * | 8/2023 | Safavi | B01L 9/543 134/22.12 |
| 2002/0063954 A1 | 5/2002 | Horton | |
| 2005/0074363 A1 | 4/2005 | Dunfee | |
| 2006/0054188 A1 * | 3/2006 | Gifford | B08B 3/12 134/166 C |
| 2006/0093530 A1 | 5/2006 | Ueda | |
| 2006/0191893 A1 | 8/2006 | Weinfield et al. | |
| 2006/0233669 A1 | 10/2006 | Panzer et al. | |
| 2009/0032064 A1 * | 2/2009 | Gifford | G01N 35/1004 134/22.12 |
| 2009/0263904 A1 * | 10/2009 | Clinton | G01N 21/69 422/52 |
| 2009/0301530 A1 | 12/2009 | Shin | |
| 2010/0037919 A1 | 2/2010 | Doebelin et al. | |
| 2011/0268627 A1 * | 11/2011 | Warhurst | B01L 3/0237 422/511 |
| 2011/0268628 A1 * | 11/2011 | Warhurst | B01L 3/0234 422/511 |
| 2011/0296931 A1 * | 12/2011 | Warhurst | B01L 3/0234 73/864.01 |
| 2011/0306051 A1 | 12/2011 | Belz et al. | |
| 2014/0000658 A1 | 1/2014 | Koehneke et al. | |
| 2014/0318574 A1 | 10/2014 | Safavi | |
| 2015/0251226 A1 | 9/2015 | Safavi | |
| 2015/0314341 A1 | 11/2015 | Safavi | |
| 2016/0016161 A1 * | 1/2016 | Schoeneck | B08B 9/023 73/863.32 |
| 2016/0101423 A1 | 4/2016 | Smith | |
| 2016/0157696 A1 | 6/2016 | Safavi et al. | |
| 2016/0296651 A1 | 11/2016 | Safavi | |
| 2016/0332155 A1 | 11/2016 | Schoeneck | |
| 2019/0076559 A1 | 3/2019 | Safavi | |
| 2019/0216290 A1 | 7/2019 | Safavi et al. | |

OTHER PUBLICATIONS

International Search Report and Written Opinion for Application No. PCT/US2016/041145, dated Sep. 22, 2016.

International Search Report and Written Opinion for Application No. PCT/US2017/016821 dated Apr. 13, 2017.

International Search Report and Written Opinion for Application No. PCT/US2014/036186, dated Aug. 5, 2014.

Product Flyer, VIAFLO 96 and VIAFLO 384-Handheld 96- and 384-channel pipette, Integra Biosciences Corp.

TipCharger Plasma Treatment System brochure, IonField Systems, undated.

TipCharger V20.06 User's Guide, IonFiled Systems, May 2013.

U.S. Restriction Requirement issued in U.S. Appl. No. 16/821,710 dated Mar. 24, 2022.

U.S. Office Action issue in U.S. Appl. No. 16/821,710 dated Sep. 29, 2022.

U.S. Notice of Allowance issued in U.S. Appl. No. 16/821,710 dated Apr. 13, 2023.

U.S. Appl. No. 16/821,710, filed Mar. 21, 2019, Ali Safavi, GRENOVA, INC.

* cited by examiner

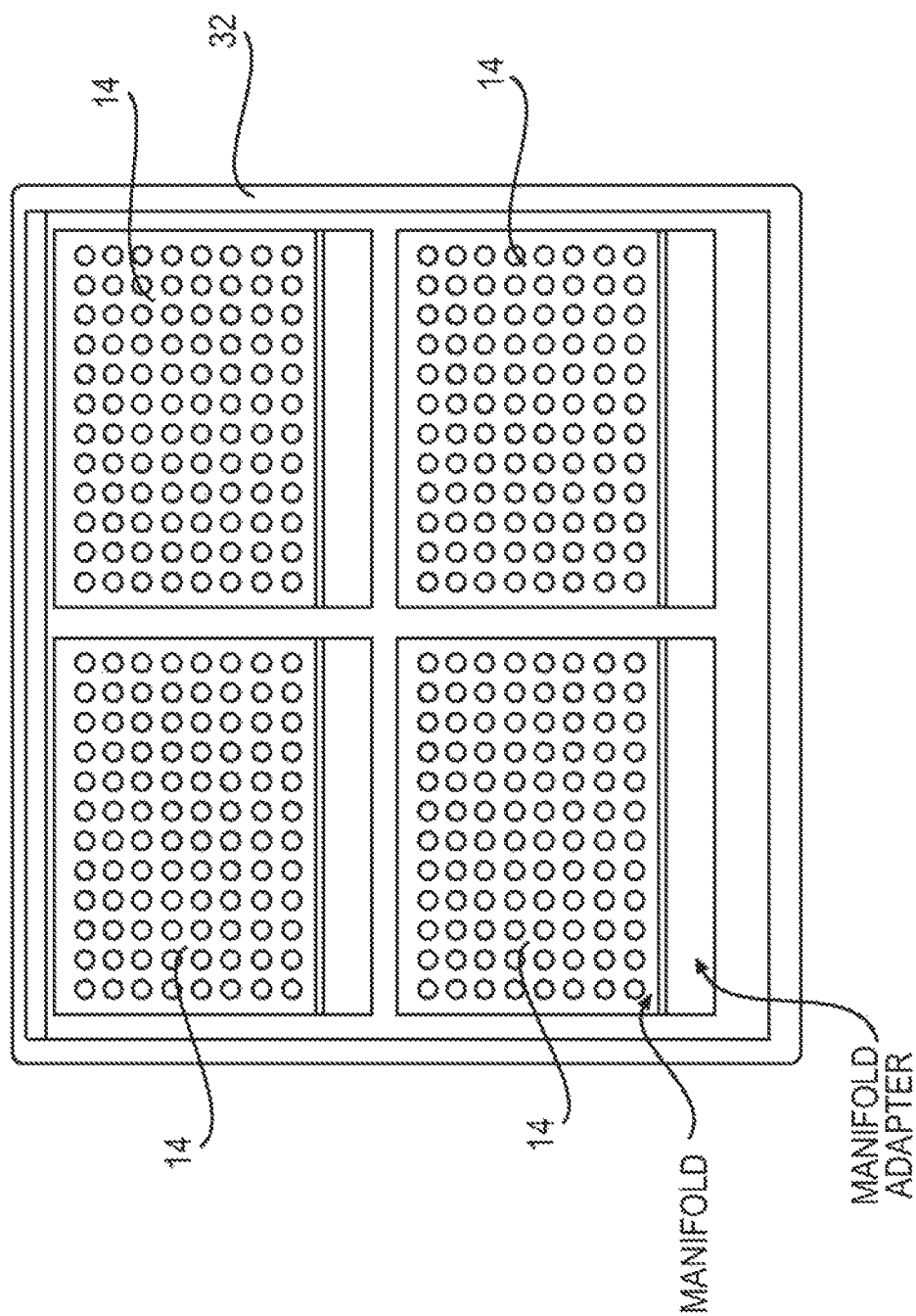

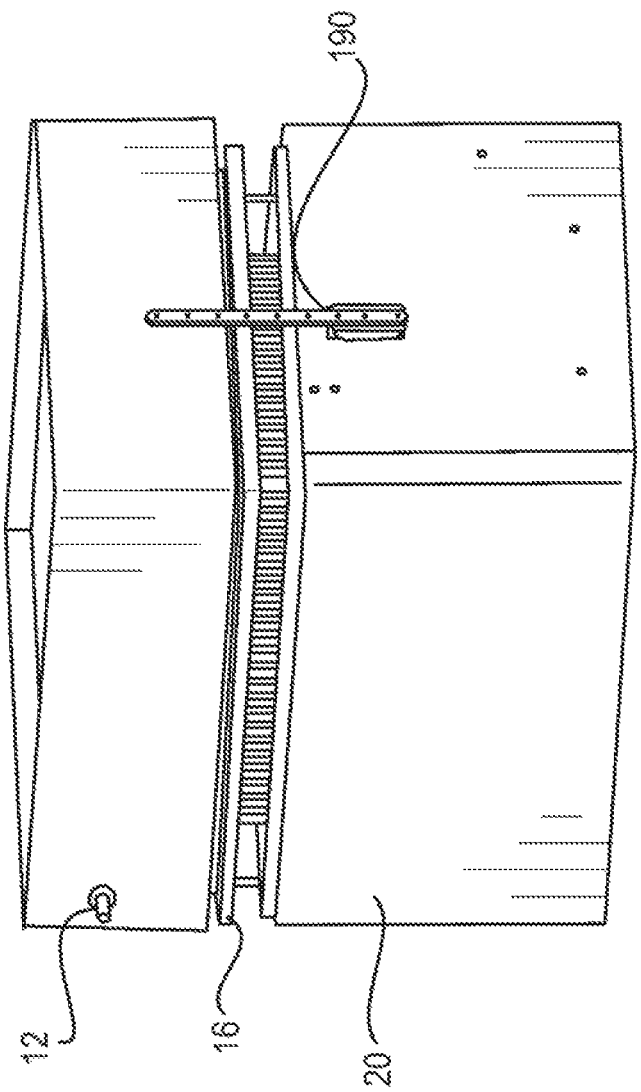

PIPETTE TIP WASHING DEVICE

CROSS-REFERENCE TO RELATED APPLICATIONS

This application is a continuation application of and claims priority to U.S. patent application Ser. No. 16/821,710 filed Mar. 17, 2020, which is a continuation of and claims priority to Ser. No. 16/361,059, filed Mar. 21, 2019, now U.S. Pat. No. 10,631,707, which in turn is a divisional of and claims priority to U.S. patent application Ser. No. 15/042,578, filed Feb. 12, 2016 and issued as U.S. Pat. No. 10,285,564 on May 14, 2019, which in turn is a continuation-in-part and claims priority to U.S. patent application Ser. No. 14/796,712, filed Jul. 10, 2015 and issued as U.S. Pat. No. 9,744,570 on Aug. 29, 2017, which in turn is a continuation-in-part and claims priority to U.S. patent application Ser. No. 14/266,330, filed Apr. 30, 2014 and issued as U.S. Pat. No. 9,421,289 on Aug. 23, 2016, which in turn claims the benefit of U.S. Provisional Patent Application Ser. No. 61/817,715, filed Apr. 30, 2013 and U.S. Provisional Patent Application Ser. No. 61/890,523, filed Oct. 14, 2013, each of which is hereby incorporated by reference in its entirety.

FIELD OF THE INVENTION

The present technology relates to a washing device and a method of washing laboratory consumables, and more particularly to a pipette tip washing device and a method of washing pipette tips.

BACKGROUND

Every year around 4,000,000 pounds of plastic pipette tips, after a single use, are disposed of in landfills globally, leading to significant environmental pollution and costs. A typical laboratory consumes several thousand pipette tips daily for samples and assay procedures. Due to the lack of options for cleaning plastic consumables, the labs discard pipette tips after each use. Such high consumption of plastic tips adds $25,000-$1.5M to the annual operation cost to each of the approximately 14,000 research laboratories in the US.

Devices that are capable of efficient pipette tip cleaning and sterilization could save businesses substantial amounts of money in their scientific operations and drastically reduce the amount of waste produced in the course of operations. Few devices have been developed for this purpose to date. In some cases, laboratories have developed small-scale cleaning methods to reuse a few pipette tips, such as single 96-tip cases. In some small-scale automatic liquid handling instruments, there are setups for the cleaning of tips with solutions. Neither of these options, however, is large enough in scale to be useful in a large industrial, government, or academic laboratory that may use hundreds of pipette tips every day. Additionally, labs must have absolute confidence that a cleaning system has completely removed all contaminants from the pipette tips so that there is no carryover, a term for the contamination presented into an experiment by equipment used in a prior experiment.

A reusable pipette tip cleaning system that uses plasmas generated above and injected through the pipette tips is disclosed in U.S. Pat. No. 8,366,871, which is hereby incorporated herein by reference in its entirety. The plasma reaches both the inside and the outside of the tip body. However, this plasma system is expensive and requires exotic equipment to produce and direct plasmas through the pipette tips. Another cleaning system is disclosed in U.S. Pat. No. 7,300,525, which is hereby incorporated herein by reference in its entirety. This cleaning system, however, involves a complex system for the cleaning of pipette probes and stirrers. This device is designed with only a single washing cavity combining multiple jet streams. There is no application to pipette tips or a design that fosters a multiplicity of cleaning units operated simultaneously.

Thus, there is a need for a large-scale and economical method for the comprehensive cleaning and sterilization of pipette tips so they may be reused in large-scale laboratory processes.

BRIEF SUMMARY

In one embodiment of the invention, a washing device comprises a manifold dispenser comprising at least one liquid input and a plurality of liquid outputs that operably direct fluid to contact a plurality of laboratory consumables held by a rack in the washing device, an ultra-violet (UV) light source, and a plurality of fiber optic channels coupled to the UV light source, each of the fiber optic channels extending into a corresponding one of the liquid outputs.

The plurality of liquid outputs may each comprise a nozzle having an opening into which a respective one of the plurality of fiber optic channels extends.

A number of liquid outputs may be equal to a number of laboratory consumables such that each one of the liquid outputs operably directs fluid at a corresponding one of the laboratory consumables.

A number of liquid outputs may be a multiple of a number of laboratory consumables such that each two or more of the liquid outputs operably directs fluid at a corresponding one of the laboratory consumables.

The manifold dispenser may be selectively movable up and down between, respectively a loading/unloading position and a washing position. Each of the liquid outputs may comprise a nozzle and encircling washer, each washer contacting a corresponding one of the laboratory consumables when the manifold dispenser is in its washing position. The washing device may further comprise a splashguard projecting downward from the manifold dispenser, the splashguard being selectively movable up and down in conjunction with the manifold dispenser, the splashguard at least partially surrounding a top edge of the rack when the manifold dispenser is in its washing position.

The washing device may comprise a first compartment and a second compartment positioned below the first compartment. The first compartment contains the manifold dispenser and the second compartment contains the laboratory consumables held by the rack. The second compartment may comprise a drawer compartment selectively movable out and in between, respectively, an open position and a closed position. The drawer compartment receives the plurality of laboratory consumables held by the rack when the drawer compartment is in its open position. The first compartment is positioned above the drawer compartment when the drawer compartment is in its closed position. The second compartment may comprise a washing chamber. The washing chamber receives the fluid operably directed by the plurality of liquid outputs of the manifold dispenser. The washing chamber further comprises a waste drain operable to dispense received fluid from the washing chamber. The second compartment may further comprise a platform for supporting the rack holding the plurality of laboratory consumables, the platform being selectively agitatable. The washing device may further comprise one or more cylinders for selectively agitating the platform. The second compartment may further comprise an adapter selectively mountable to the platform, the adapter defining one or more openings for suspending the rack. The second compartment may further comprise a splashguard projecting upward from the platform.

The washing device may further comprise a UV curtain that directs UV light onto the plurality of laboratory consumables as the plurality of laboratory consumables moves relative to the UV curtain or as the UV curtain moves relative to the plurality of laboratory consumables. The washing device may further comprise a bottom compartment positioned below the drawer compartment when the drawer compartment is in its closed position, the bottom compartment containing an ultra-violet (UV) light source, wherein the washing chamber has a floor comprising a material transparent to UV light and wherein the UV light source is capable of outputting UV light in the direction of the washing chamber and through the floor of and into the washing chamber.

The manifold dispenser may comprise a flexible mat affixed to a bottom surface of the manifold dispenser, the mat having a plurality of through-holes defined therein. Each of the plurality of through-holes is aligned with a corresponding one of the plurality of liquid outputs such that the fluid operably directed by the fluid outputs passes through a corresponding one of the plurality of through-holes.

The rack may comprise a tip rack and the plurality of laboratory consumables comprises a plurality of pipette tips.

The washing device may further comprise a plurality of manifold dispensers, each of the manifold dispensers operably direct fluid to contact a respective plurality of laboratory consumables held by a respective rack in the washing device.

The washing device may further comprise one or more transducers capable of outputting sound in an ultrasonic range into the washing device.

In addition to the washing device, as described above, other aspects of the present invention are directed to corresponding methods for washing laboratory consumables. In one such alternative embodiment of the invention, a method for washing laboratory consumables comprises receiving, in a washing device (the washing device comprising a manifold dispenser comprising at least one liquid input and a plurality of liquid outputs that operably direct fluid to contact a plurality of laboratory consumables held by a rack in the washing device, an ultra-violet (UV) light source, and a plurality of fiber optic channels coupled to the UV light source, each of the fiber optic channels extending into a corresponding one of the liquid outputs) a rack holding a plurality of laboratory consumables; directing one or more fluid solutions to contact the plurality of laboratory consumables, the directing comprising introducing the one or more liquid solutions into the liquid input and out of the plurality of liquid outputs of the manifold dispenser; and exposing at least an interior portion of the each of the plurality of laboratory consumables to the UV light via the plurality of fiber optic channels.

The plurality of liquid outputs may each comprise a nozzle having an opening into which a respective one of the plurality of fiber optic channels extends.

A number of liquid outputs may be equal to a number of laboratory consumables such that each one of the liquid outputs directs fluid at a corresponding one of the laboratory consumables.

A number of liquid outputs may be a multiple of a number of laboratory consumables such that each two or more of the liquid outputs directs fluid at a corresponding one of the laboratory consumables.

The manifold dispenser may be selectively movable up and down between, respectively a loading/unloading position and a washing position. The method may further comprise moving the manifold dispenser downward from its loading/unloading position to its washing position prior to the directing, and moving the manifold dispenser upward from its washing position to its loading/unloading position after the directing. Each of the liquid outputs may comprise a nozzle and encircling washer, each washer contacting a corresponding one of the laboratory consumables when the manifold dispenser is in its washing position. The method may further comprise moving a splashguard downward in conjunction with moving the manifold dispenser downward from its loading/unloading position to its washing position, the splashguard projecting downward from the manifold dispenser and at least partially surrounding a top edge of the rack when the manifold dispenser is in its washing position, and moving the splashguard upward in conjunction with moving the manifold dispenser from its washing position to its loading/unloading position.

The washing device may further comprise a first compartment and a second compartment positioned below the first compartment, wherein the first compartment contains the manifold dispenser and the second compartment contains the laboratory consumables held by the rack. The second compartment may comprise a drawer compartment selectively movable out and in between, respectively, an open position and a closed position. The drawer compartment receives the plurality of laboratory consumables held by the rack when the drawer compartment is in its open position. The first compartment is positioned above the drawer compartment when the drawer compartment is in its closed position.

The second compartment may comprise a washing chamber. The washing chamber receives the fluid operably directed by the plurality of liquid outputs of the manifold dispenser. The washing chamber further comprises a waste drain operable to dispense received fluid from the washing chamber.

The second compartment may further comprise a platform for supporting the rack holding the plurality of laboratory consumables, the platform being selectively agitatable. The method may further comprise agitating the platform. The washing device may further comprise one or more cylinders for selectively agitating the platform. The second compartment may further comprise an adapter selectively mountable to the platform, the adapter defining one or more openings for suspending the rack. The second compartment may further comprise a splashguard projecting upward from the platform.

The method may further comprise moving the plurality of laboratory consumables relative to a UV light curtain or moving the UV light curtain relative to the plurality of laboratory consumables, and directing UV light from the UV light curtain onto the plurality of laboratory consumables as the plurality of laboratory consumables moves relative to the UV curtain or as the UV curtain moves relative to the plurality of laboratory consumables.

The washing device may further comprise a bottom compartment positioned below the drawer compartment when the drawer compartment is in its closed position, the bottom compartment containing a UV light source, and a floor comprising a material transparent to UV light. The method may further comprise outputting UV light in the direction of the washing chamber and through the floor of and into the washing chamber.

The manifold dispenser may comprise a flexible mat affixed to a bottom surface of the manifold dispenser, the mat having a plurality of through-holes defined therein. Each of the plurality of through-holes is aligned with a corresponding one of the plurality of liquid outputs such that the fluid operably directed by the fluid outputs passes through a corresponding one of the plurality of through-holes.

The rack may comprise a tip rack and the plurality of laboratory consumables comprise a plurality of pipette tips.

The washing device may further comprise a plurality of manifold dispensers. The directing may comprise introducing the one or more liquid solutions into the liquid input and out of the plurality of liquid outputs of each manifold dispenser such that each of the manifold dispensers directs fluid to contact a respective plurality of laboratory consumables held by a respective rack in the washing device.

The washing device may further comprise one or more transducers capable of outputting sound in an ultrasonic range into the washing device.

BRIEF DESCRIPTION OF THE SEVERAL VIEWS OF THE DRAWING(S)

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings:

FIG. 5A-5D are an exploded perspective view, a top perspective view, a side view, and a bottom view, respectively, of the top compartment of the pipette tip washing device and manifold dispensers configured to be located in the top compartment.

Figure 6A:
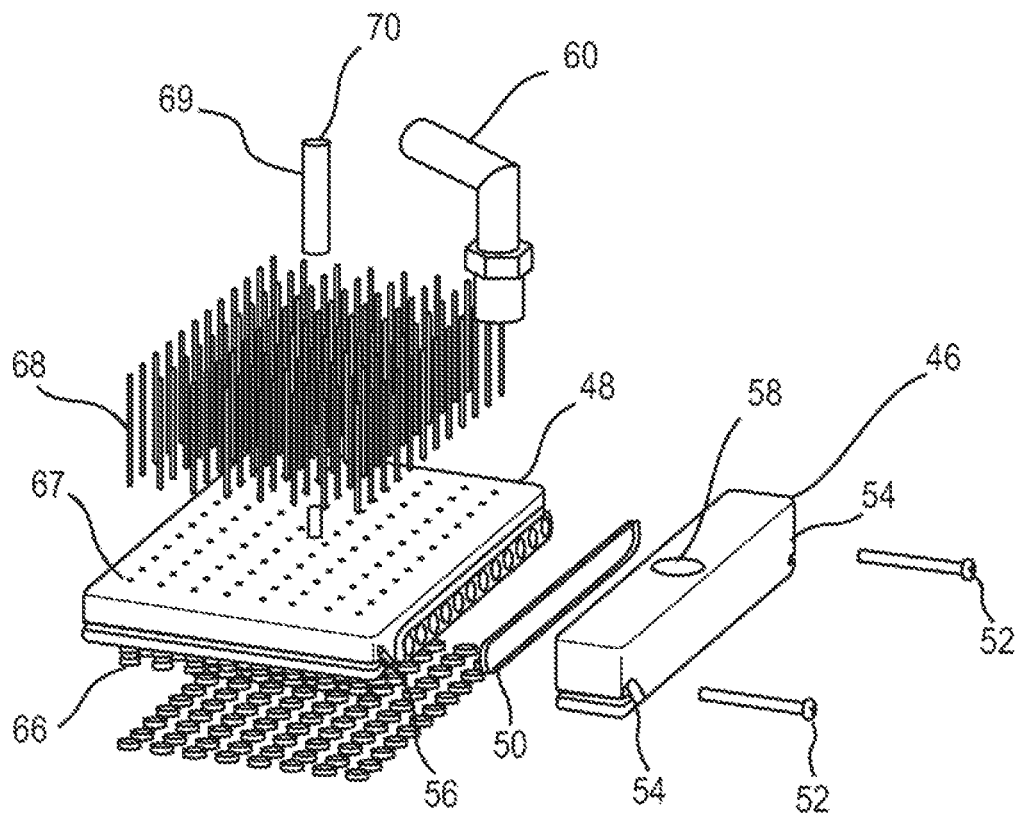
FIG. 6A is an exploded perspective view of a manifold dispenser of the present invention.
Figure 6B:
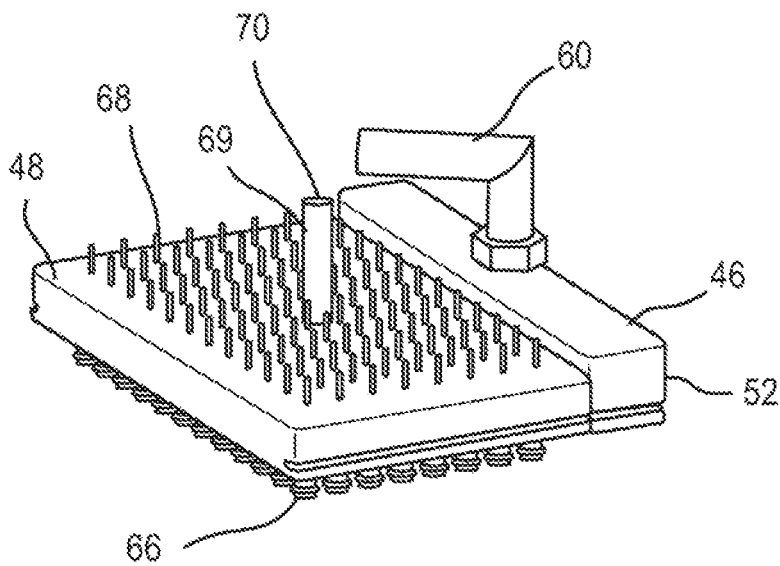
FIG. 6B is a top perspective view of the manifold dispenser of the present invention.
Figure 6C:
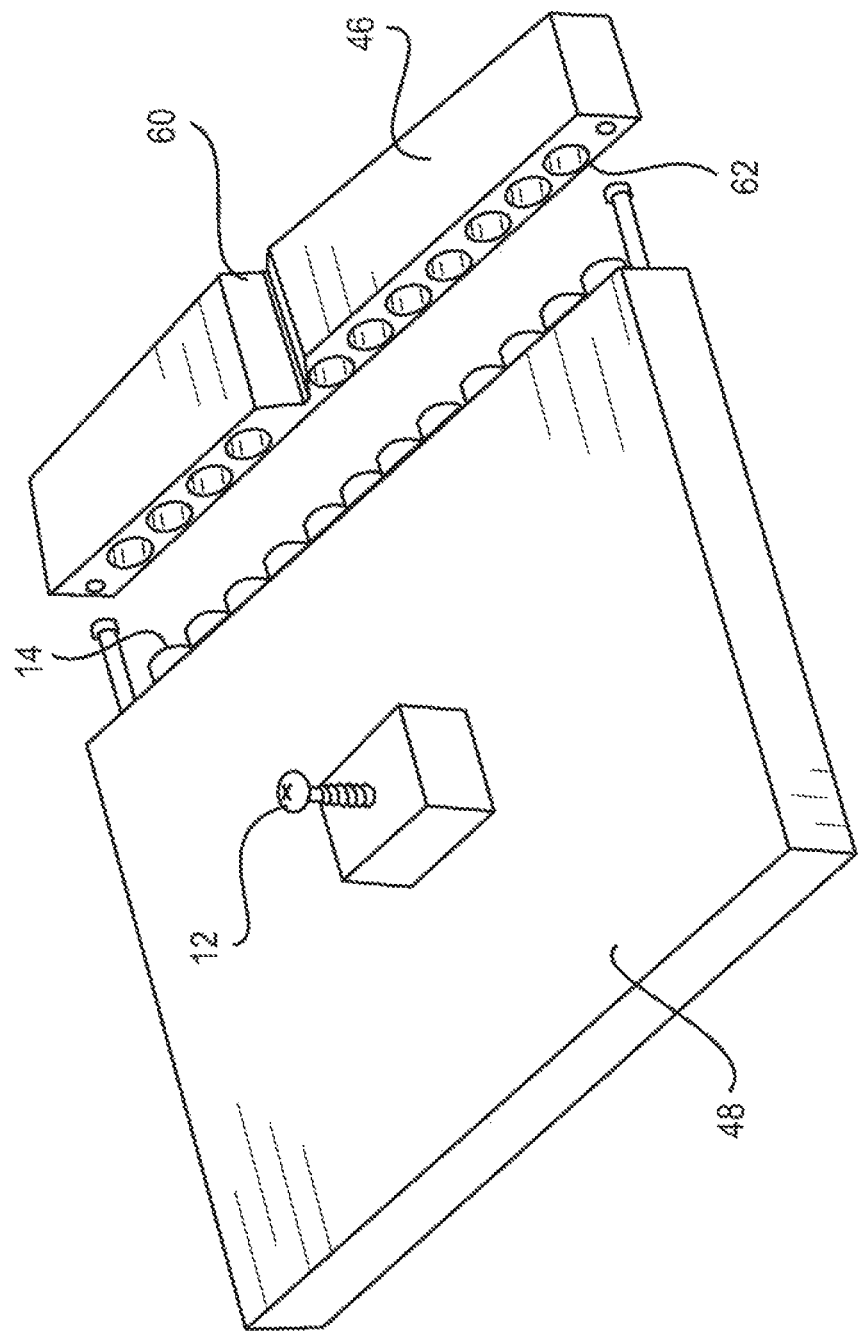

FIG. 6C an exploded view of a manifold dispenser of the present invention.

Figure 6D:
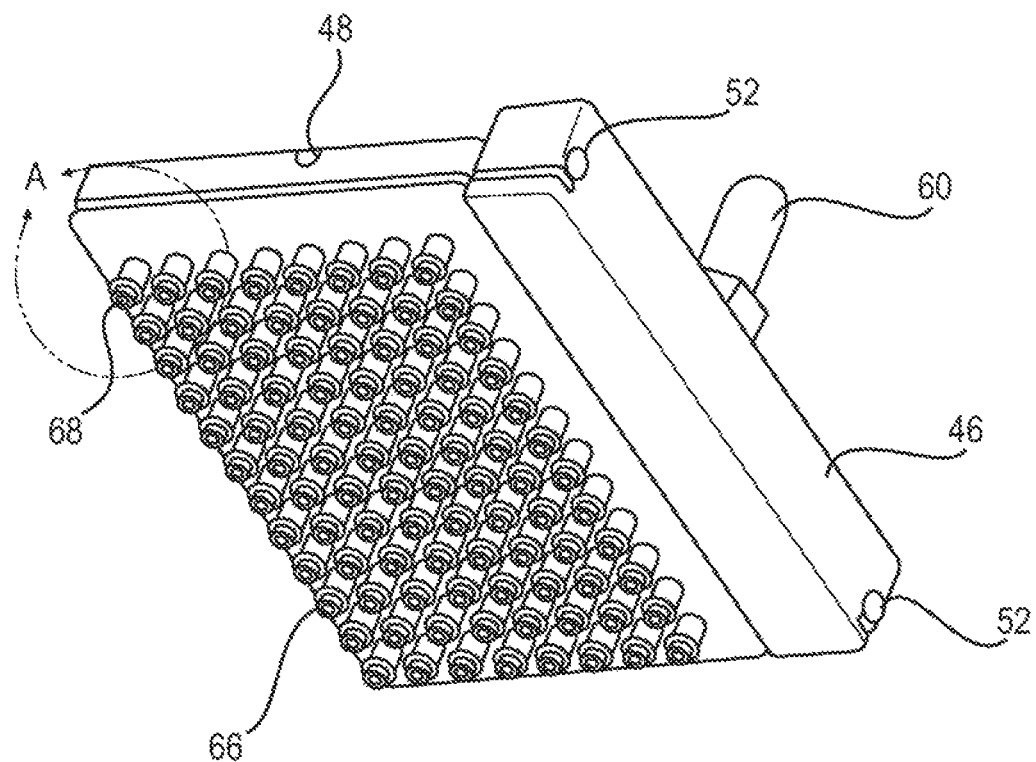

FIG. 6D is a bottom perspective view of the manifold dispenser of the present invention.

Figure 6E:
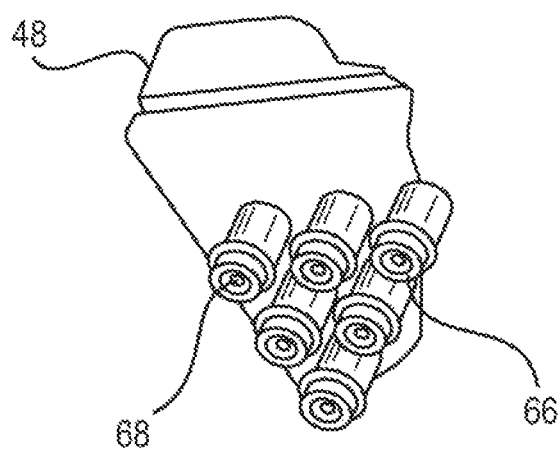
Figure 7A:
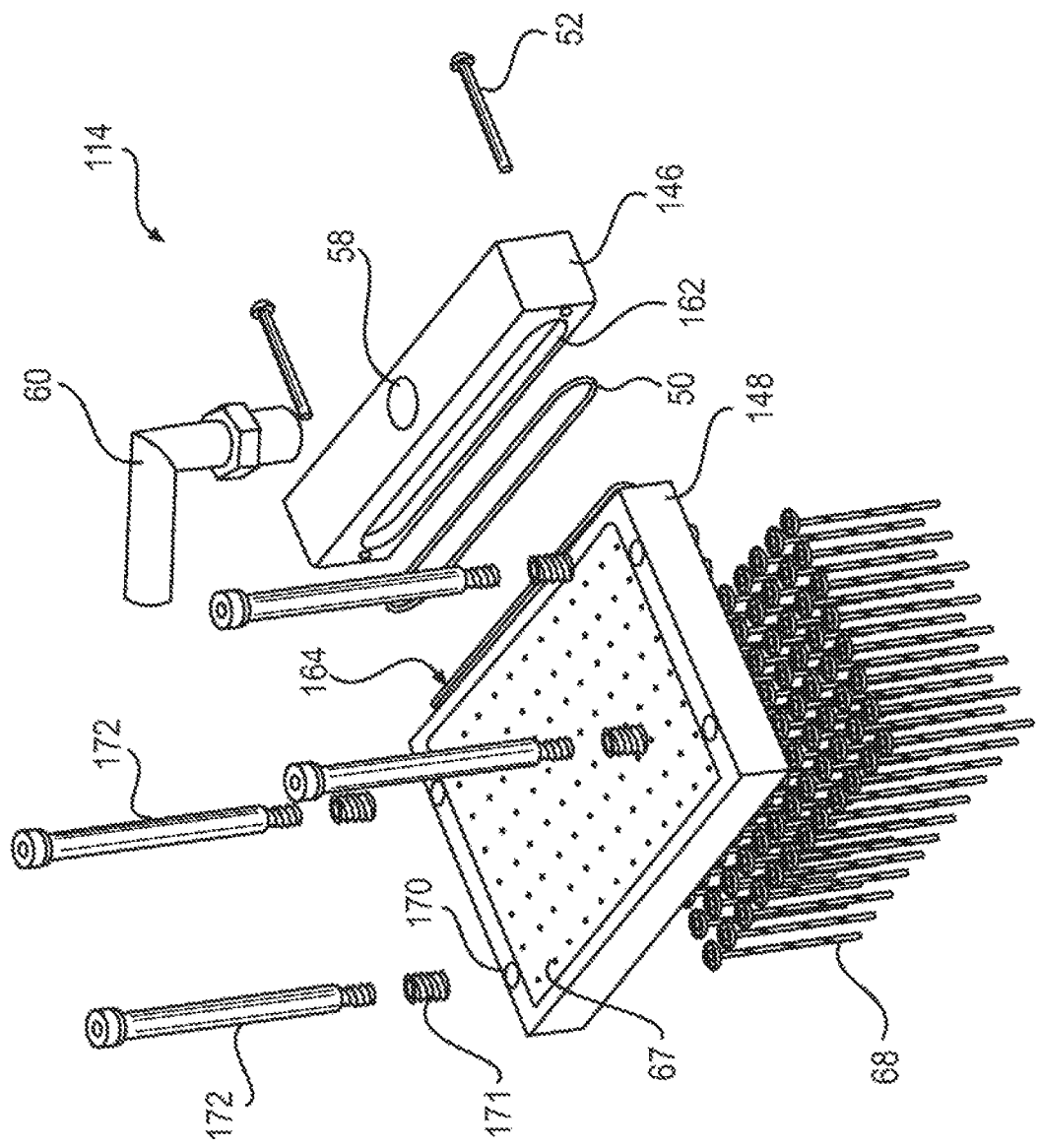
Figure 7B:
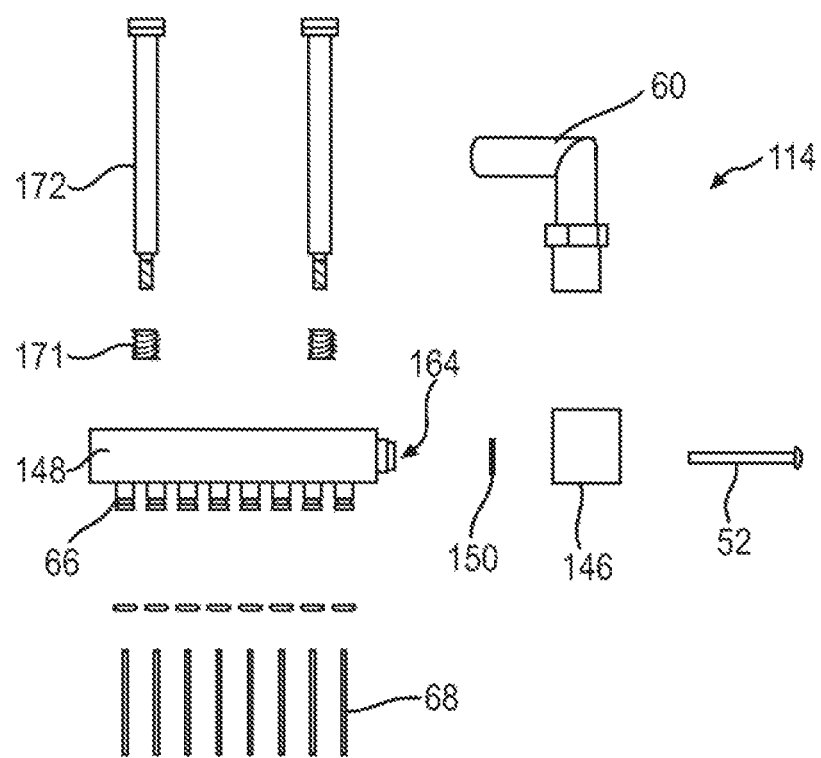

FIG. 6E is a magnified view of portion A of the manifold dispenser illustrated in FIG. 6D FIGS. 7A and 7B are an exploded perspective view and an exploded side view of another embodiment of the manifold dispenser of the present invention.

Figure 8A:
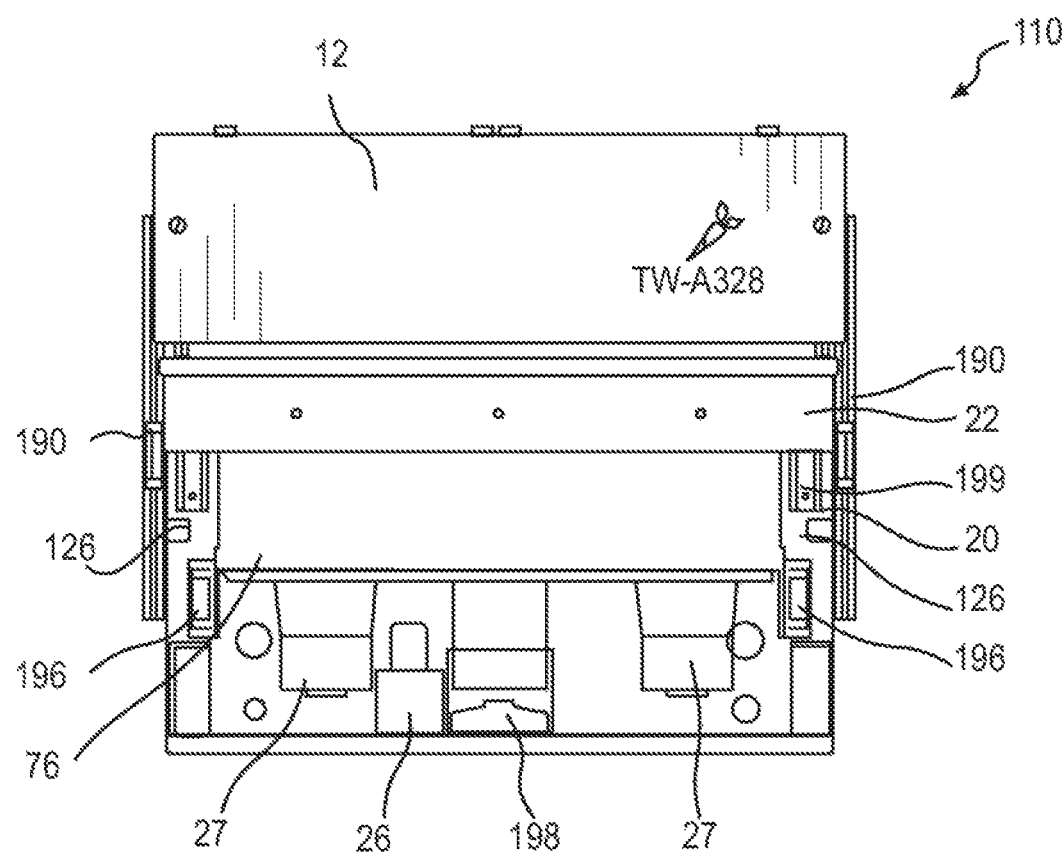
Figure 8B:
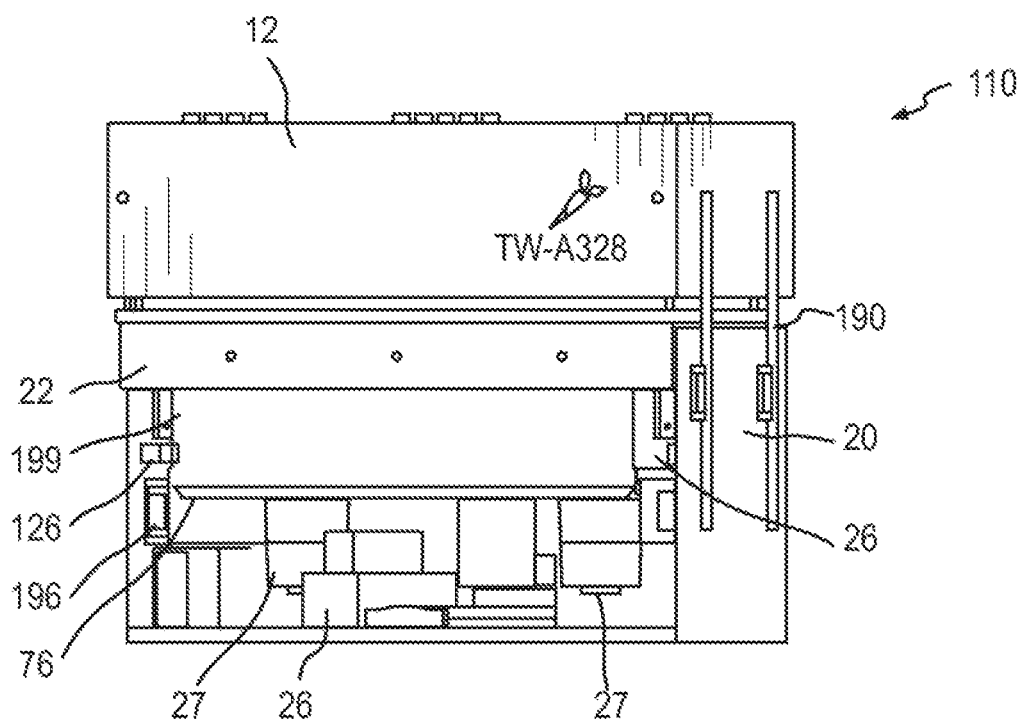

FIGS. 8A and 8B are partial phantom front and perspective views of another exemplary embodiment of a pipette tip washing device of the present disclosure.

Figure 8C:
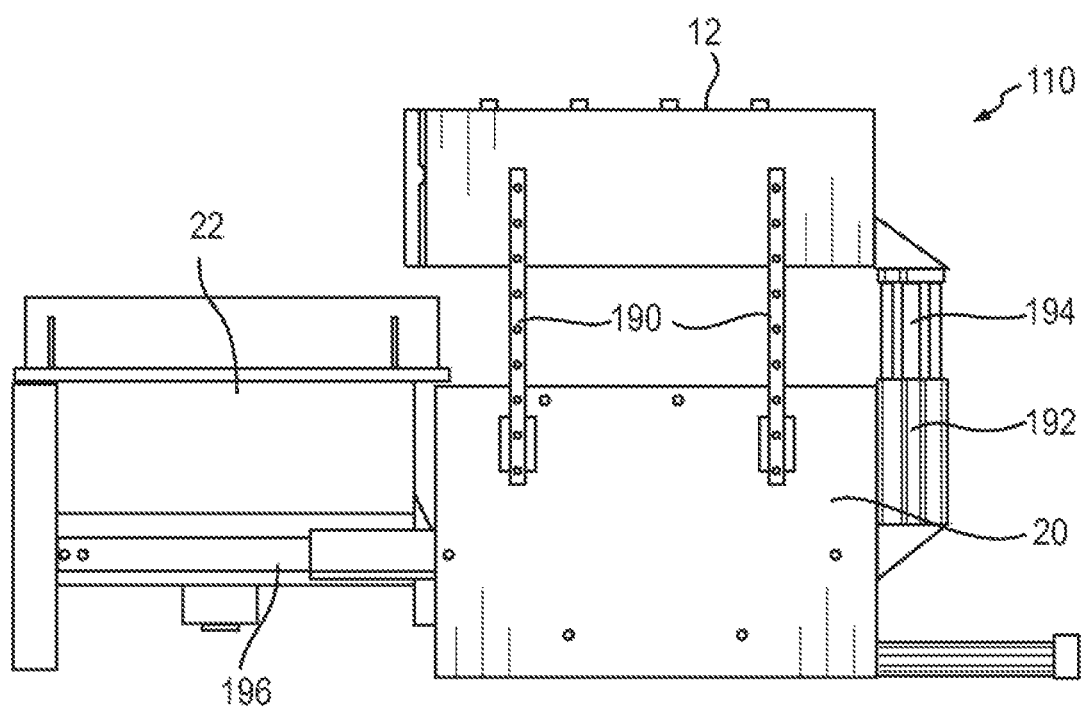

FIG. 8C is a side view of the pipette tip washing device illustrated in FIGS. 8A and 8B in an opened position.

FIGS. 9A-9D are perspective views of the pipette tip washing device illustrated in FIGS. 8A-8C in various positions during operation of the device in accordance with the present disclosure.

Figure 10:
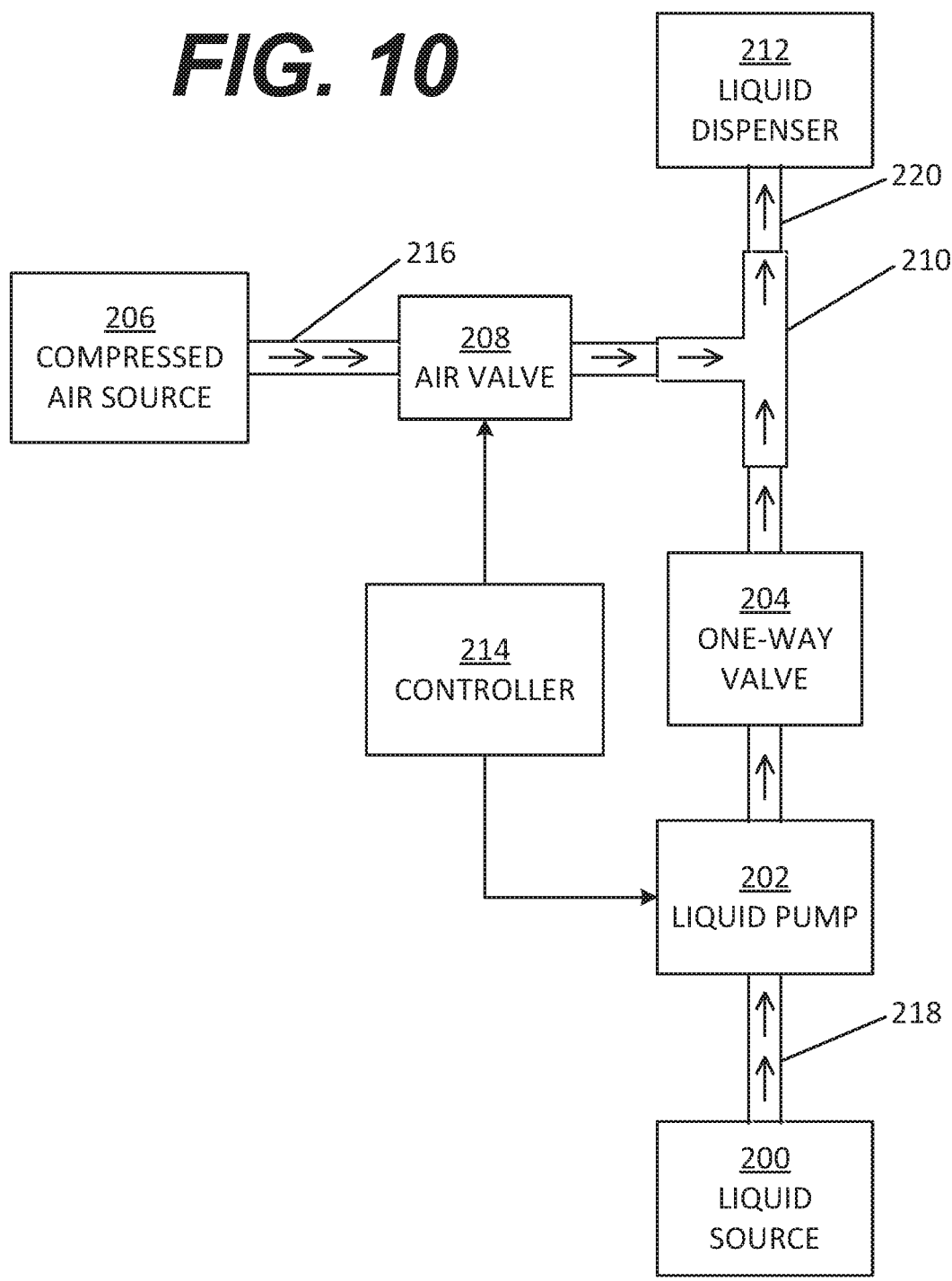

FIG. 10 is a block diagram of a liquid and air supply portion of the present invention.

Figure 11:
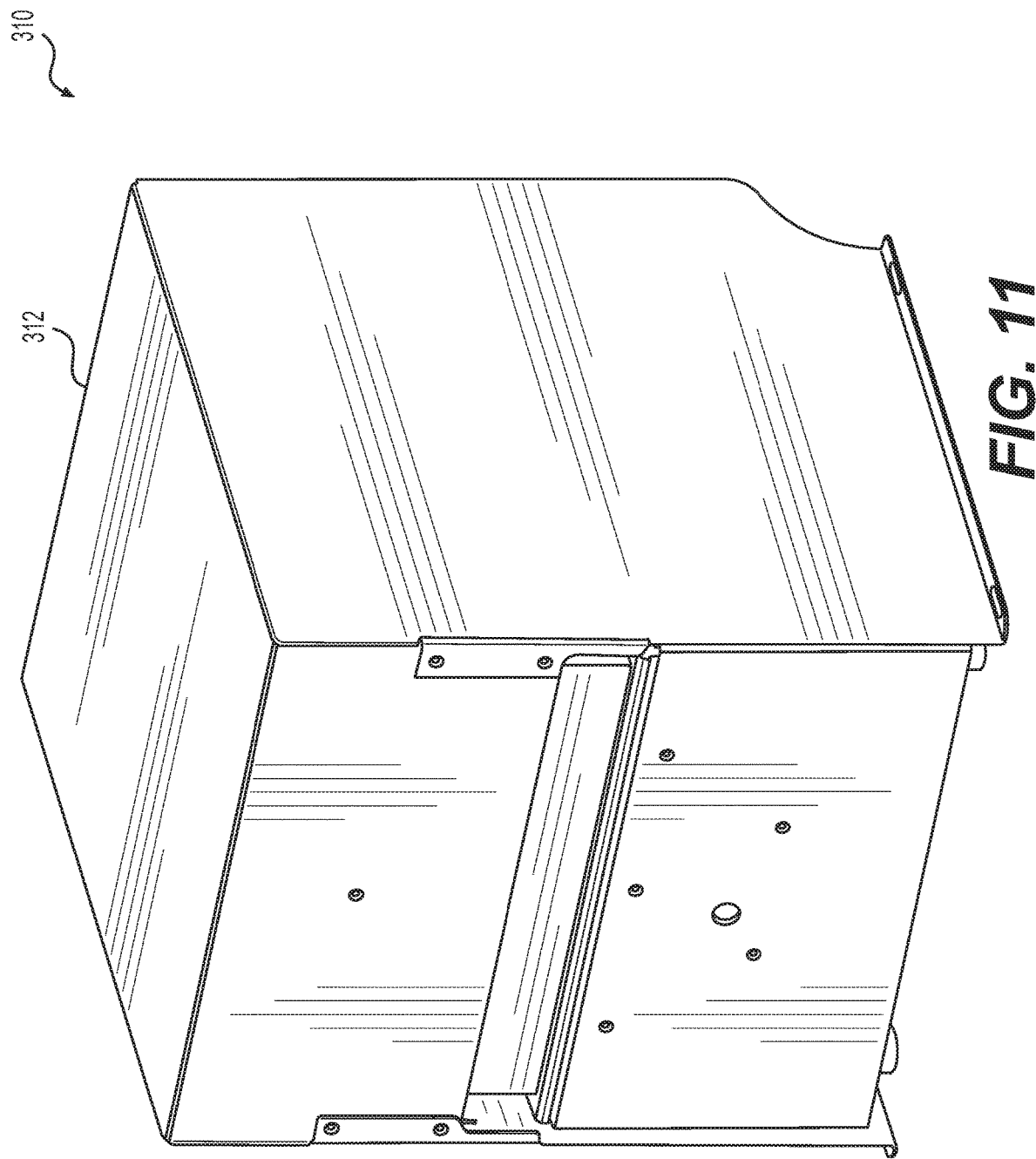

FIG. 11 is a perspective view of another embodiment of a pipette tip washing device of the present disclosure, showing the drawer compartment closed.

Figure 12:
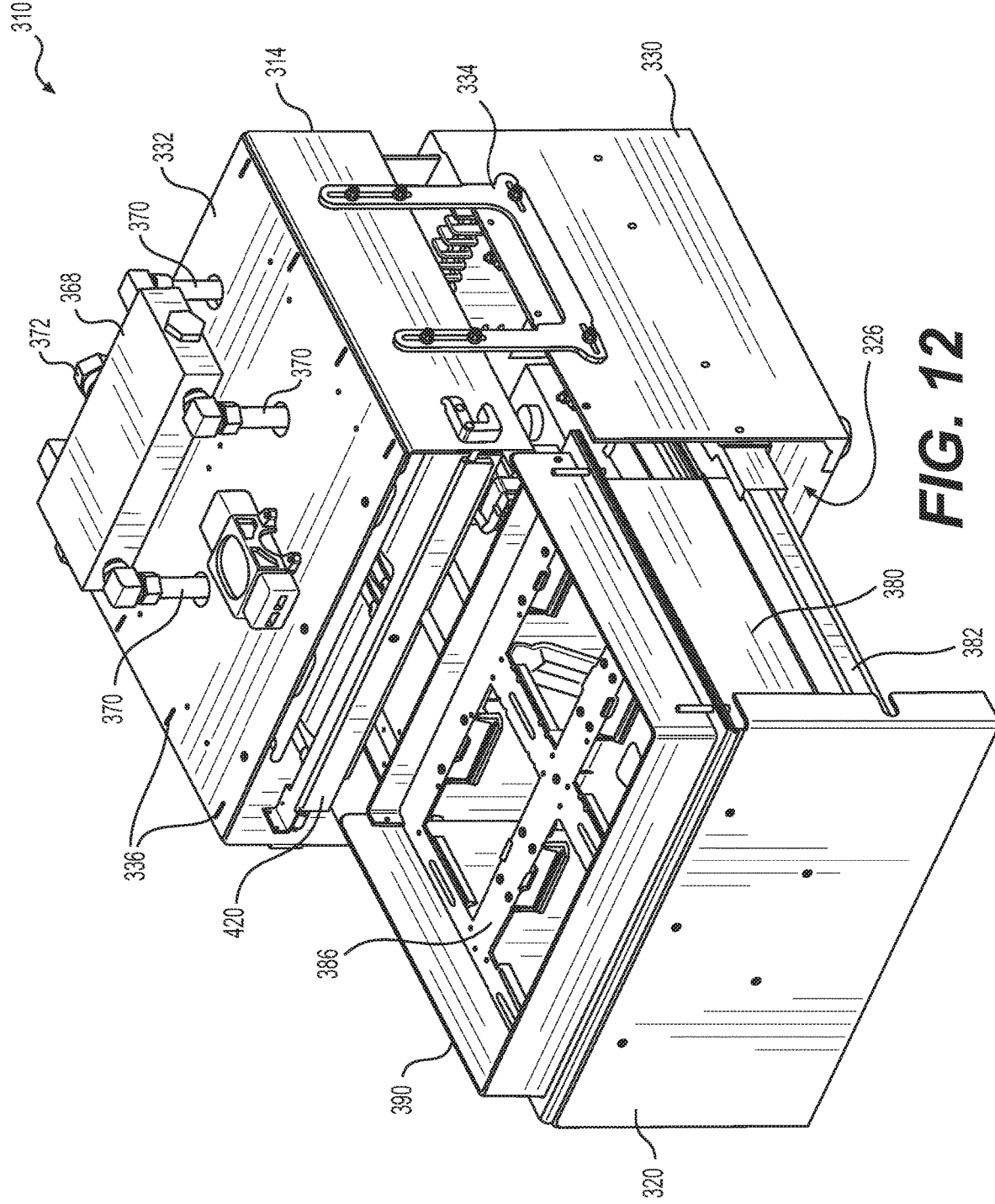
Figure 13:
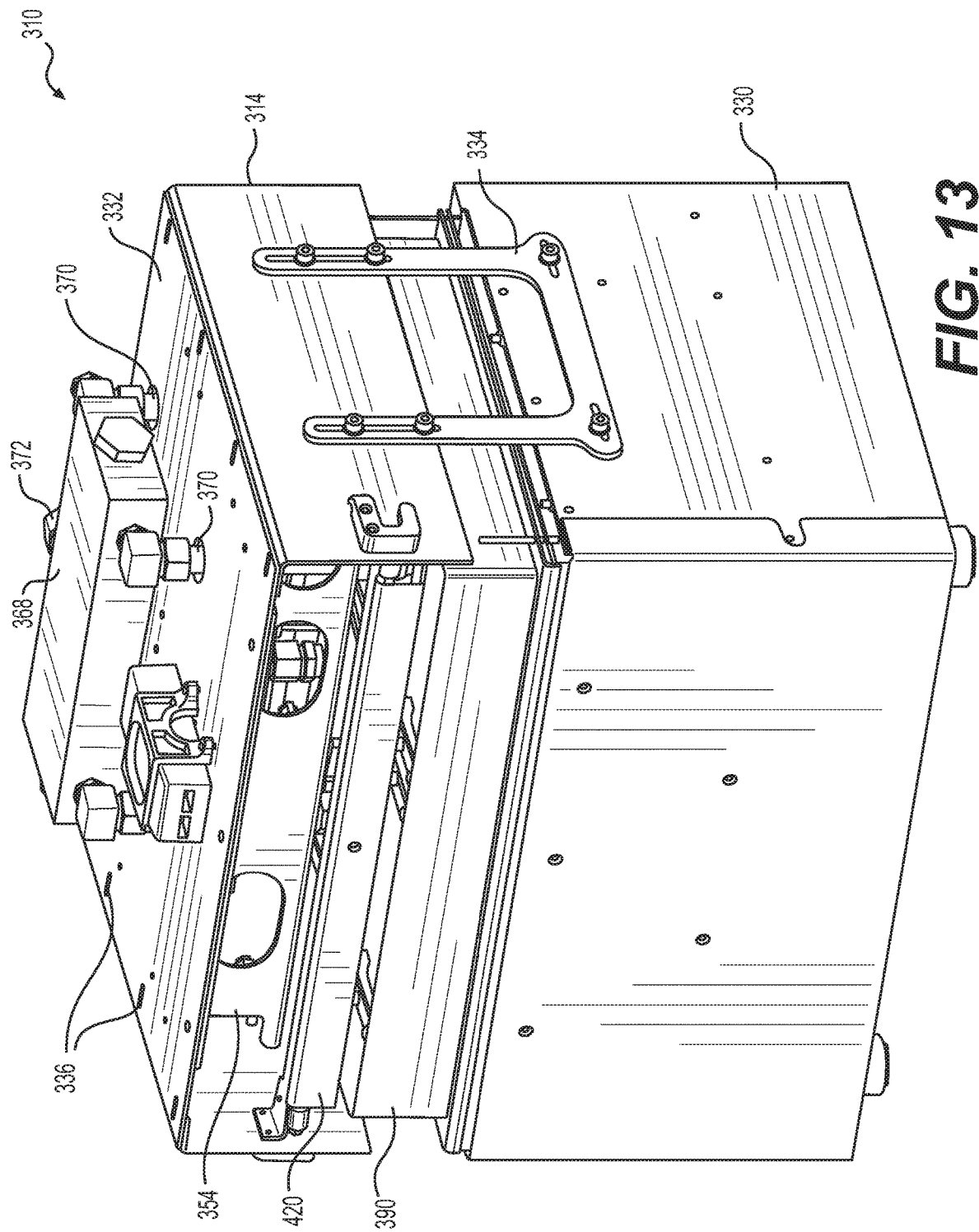

FIGS. 12 and 13 are perspective views of the pipette tip washing device illustrated in FIG. 11, showing the drawer compartment, respectively, open and closed, and the outer shell removed for visibility of the internal components.

Figure 14:
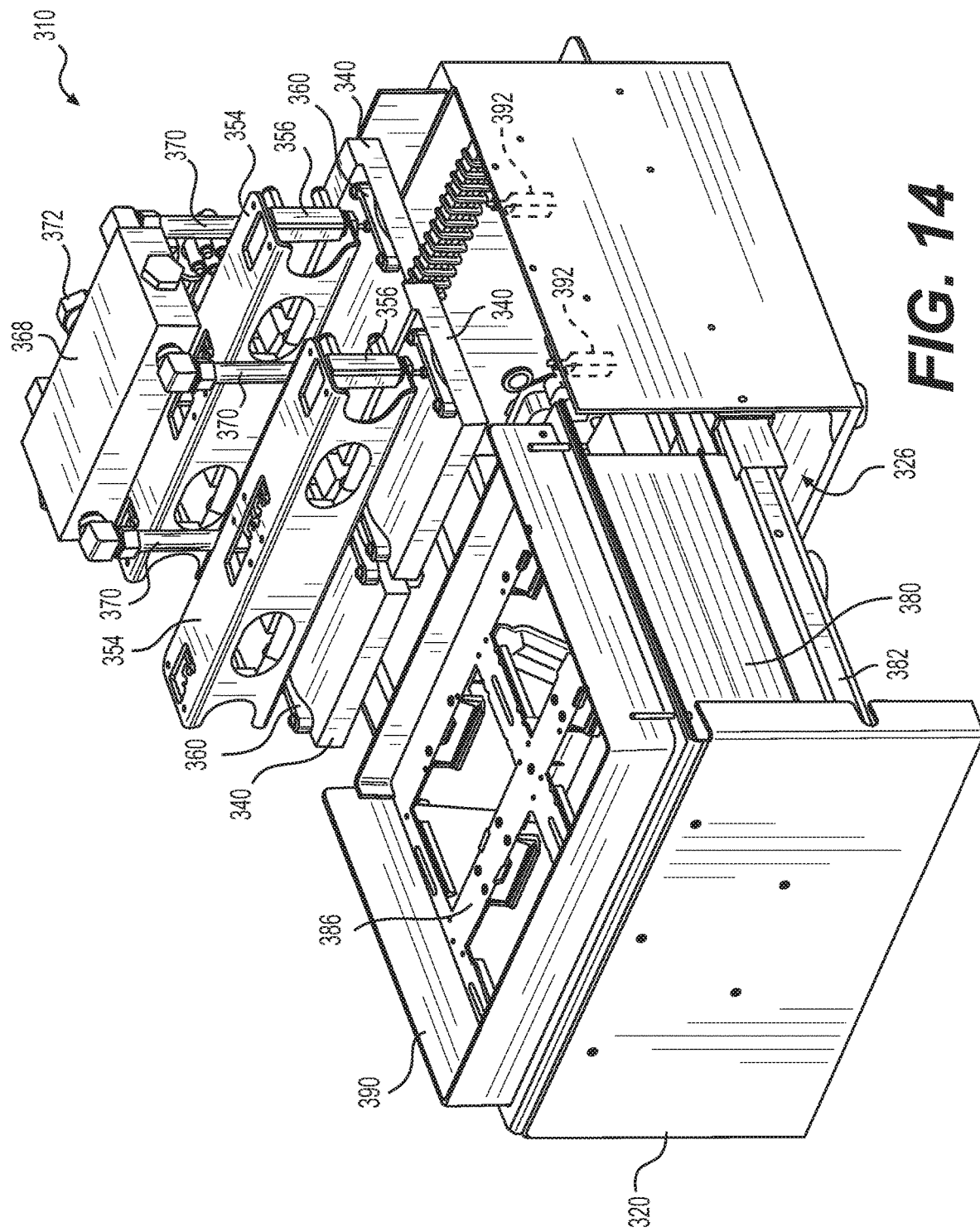

FIG. 14 is a perspective view of the pipette tip washing device illustrated in FIG. 11, with the outer shell and some inner walls removed for visibility of the internal components.

Figure 15:
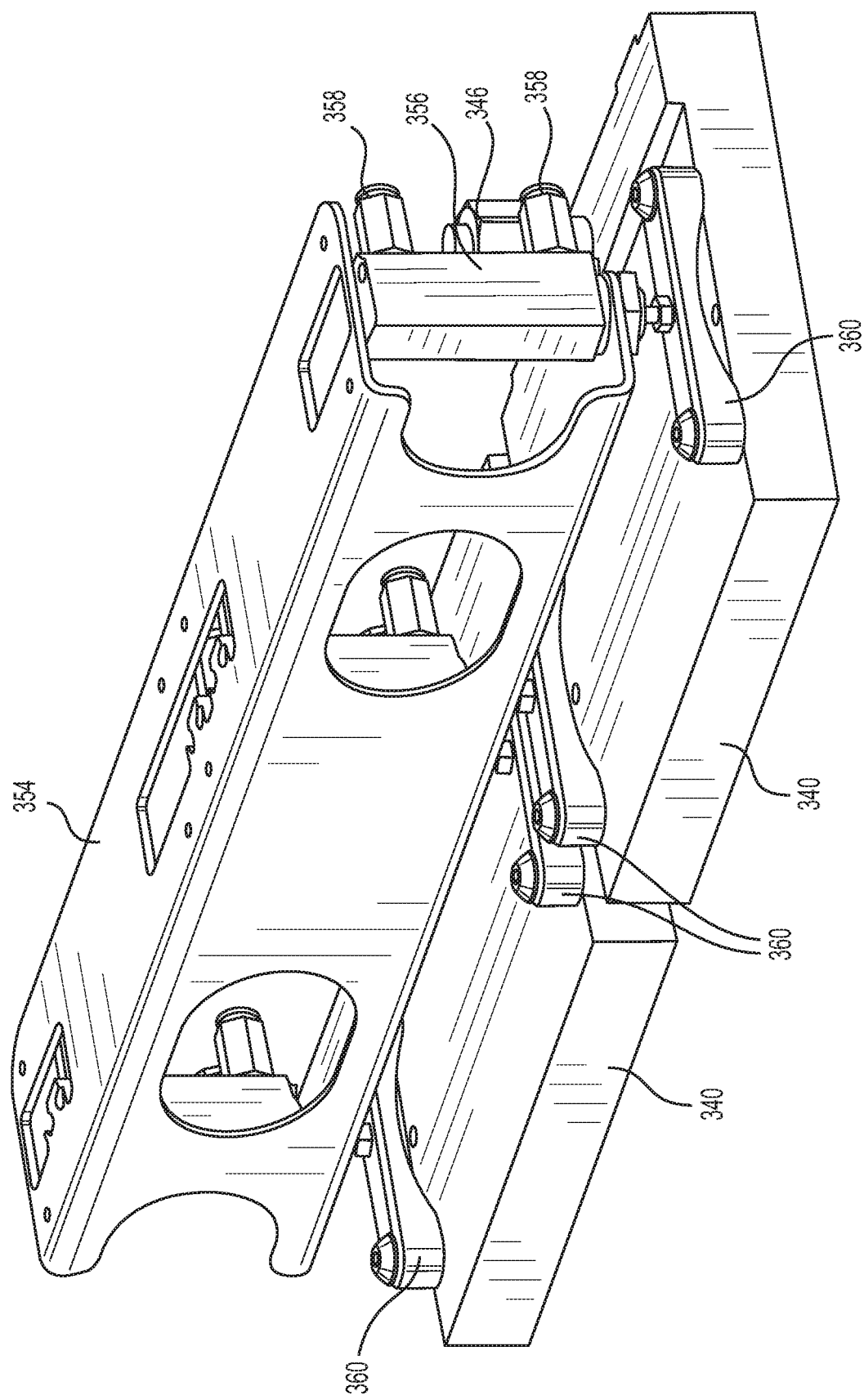
Figure 16:
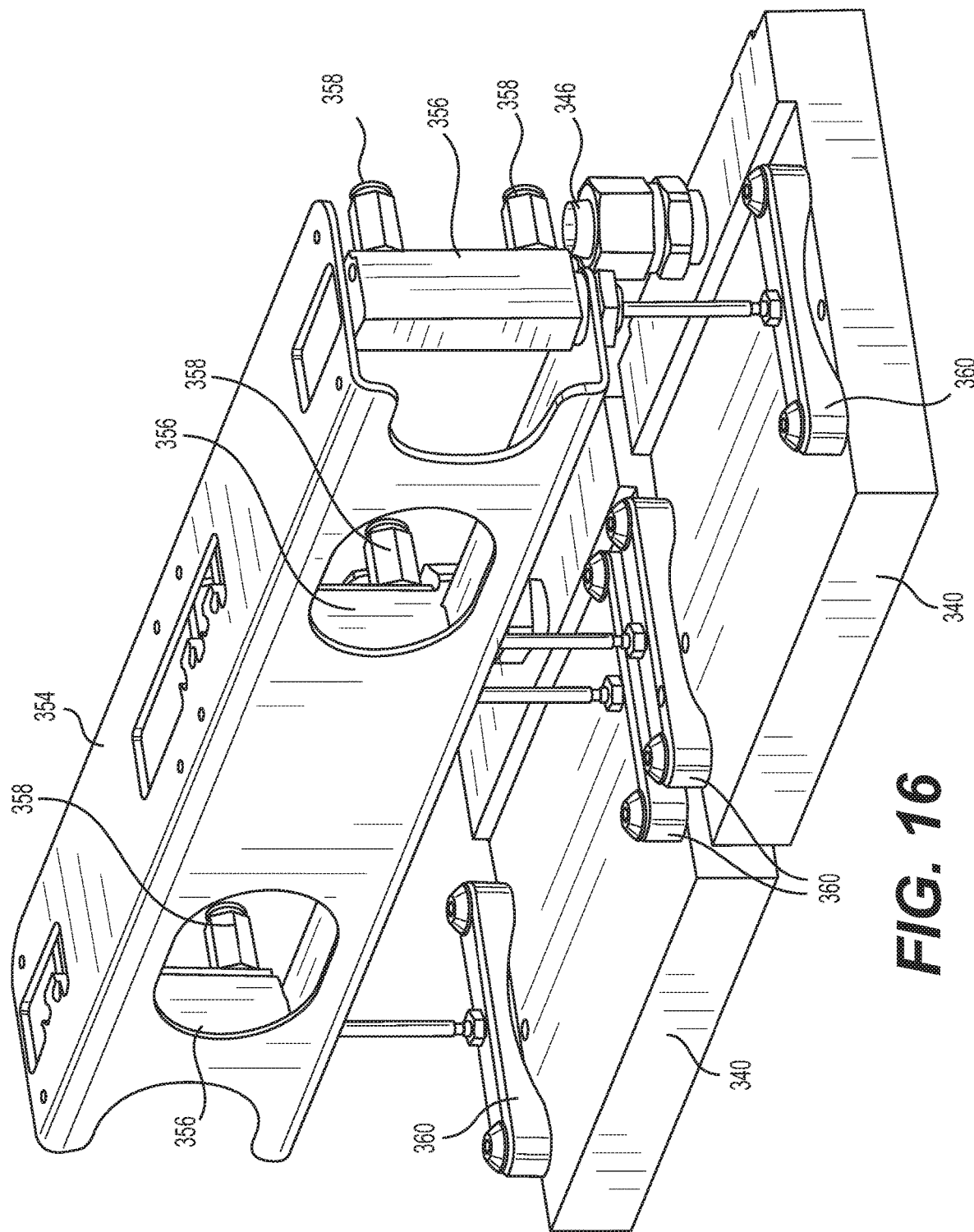

FIGS. 15 and 16 are perspective views of the manifold support beam and manifold dispenser removed from the pipette tip washing device illustrated in FIG. 11, in, respectively, a retracted and extended position.

Figure 17:
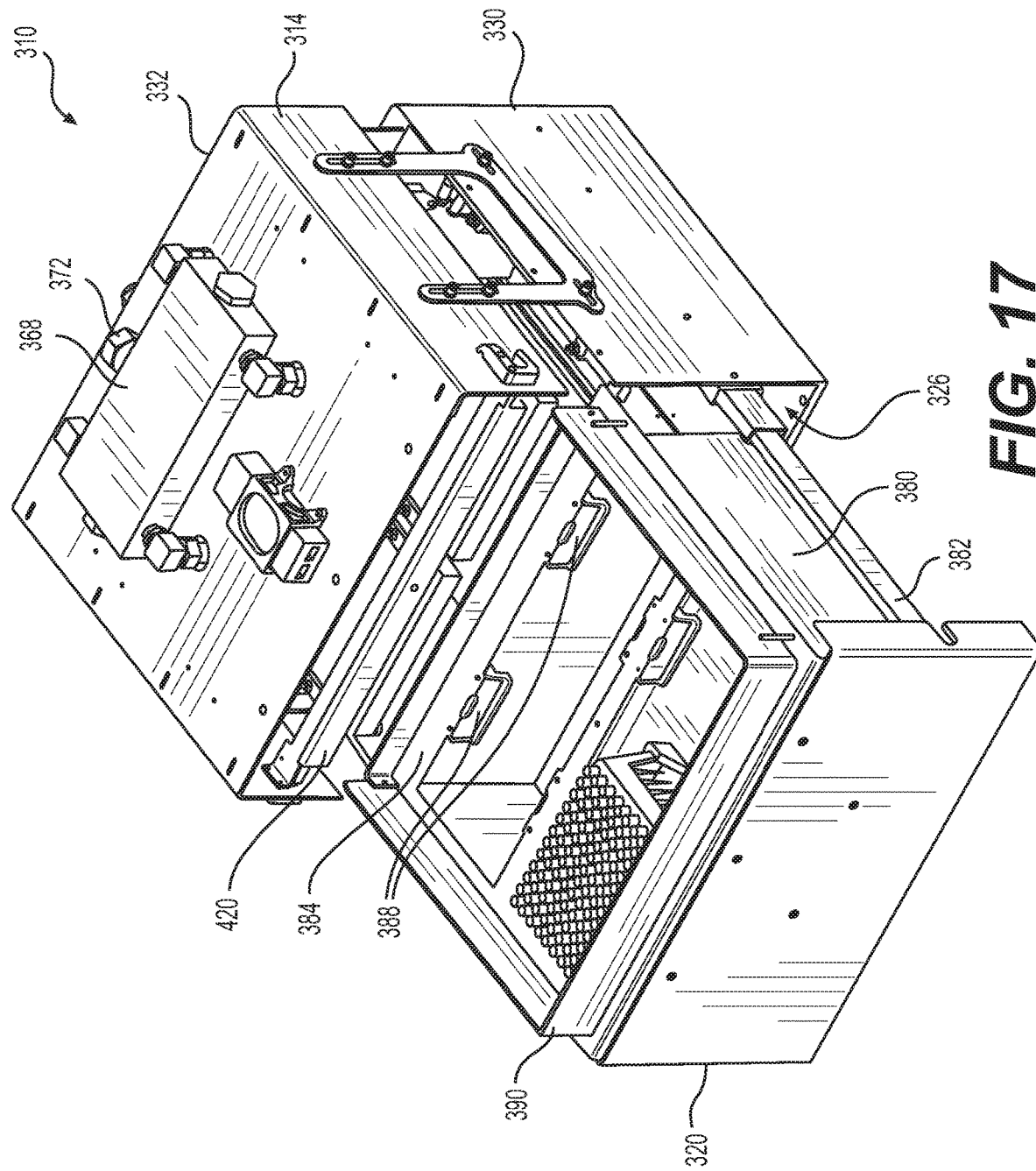

FIG. 17 is a perspective view of the pipette tip washing device illustrated in FIG. 11, with a tip rack adapter removed.

Figure 18:
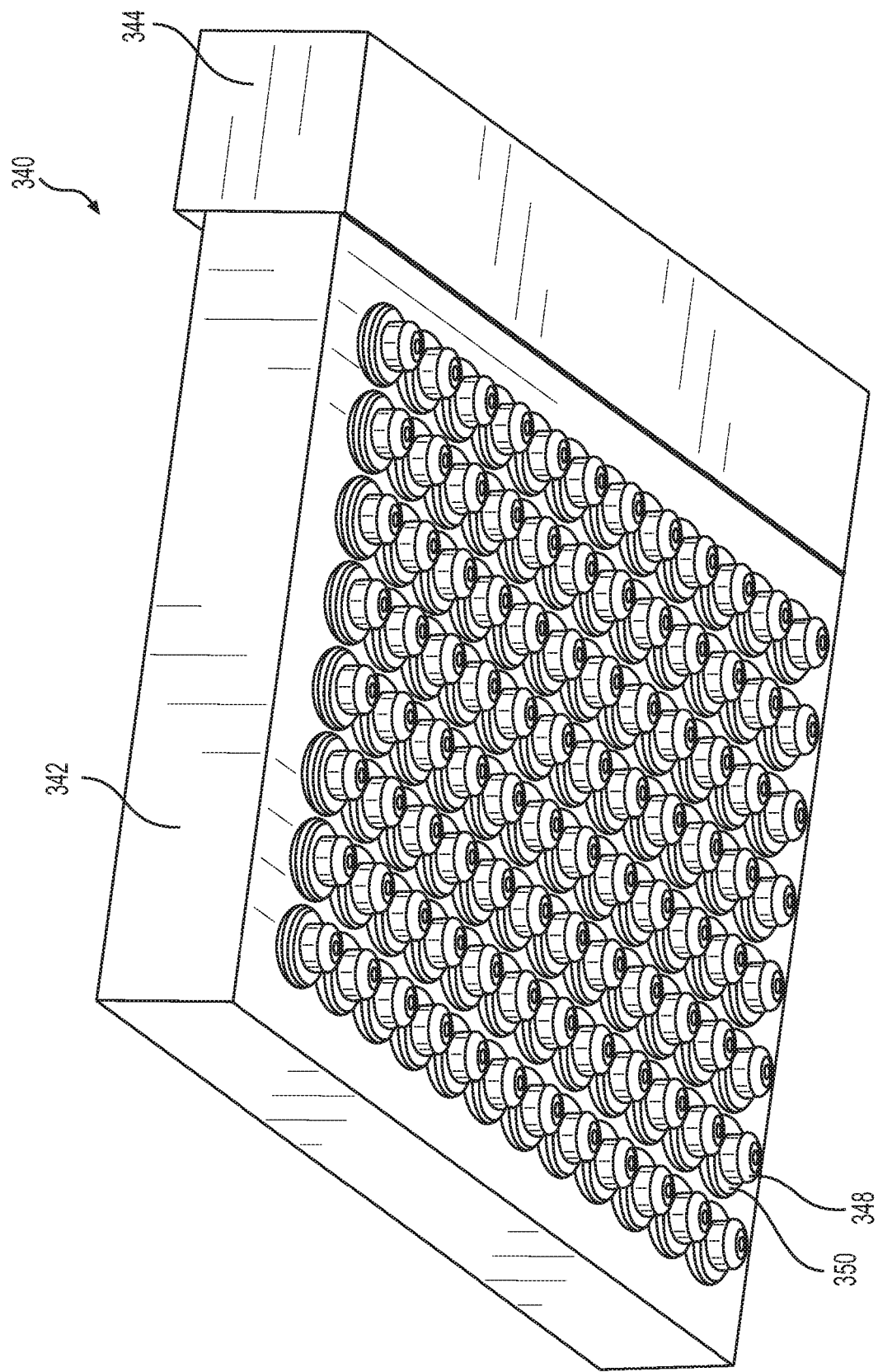

FIG. 18 is a perspective view of another embodiment of the manifold dispenser of the present invention.

Figure 19:
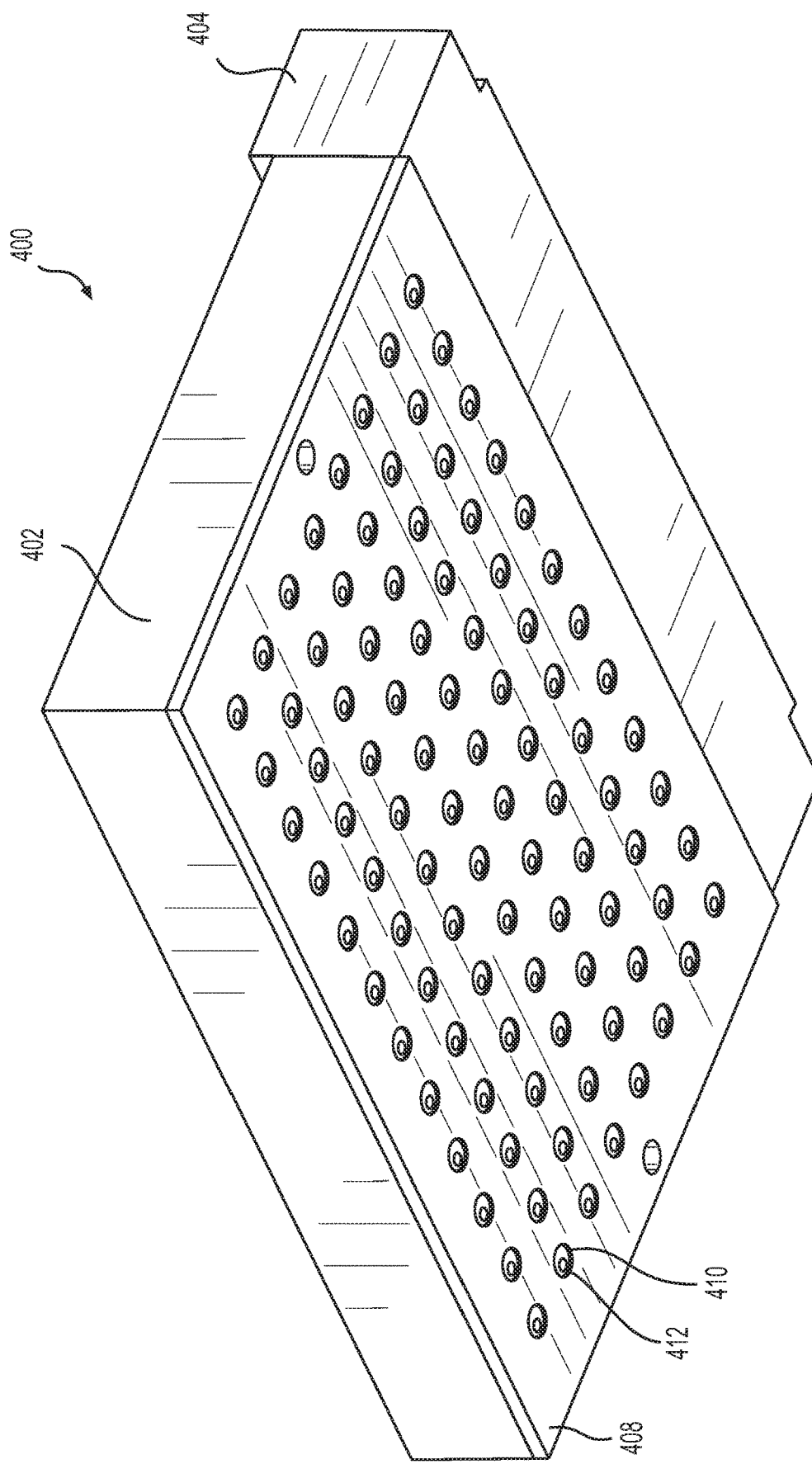

FIG. 19 is a perspective view of another embodiment of the manifold dispenser of the present invention.

Figure 20:
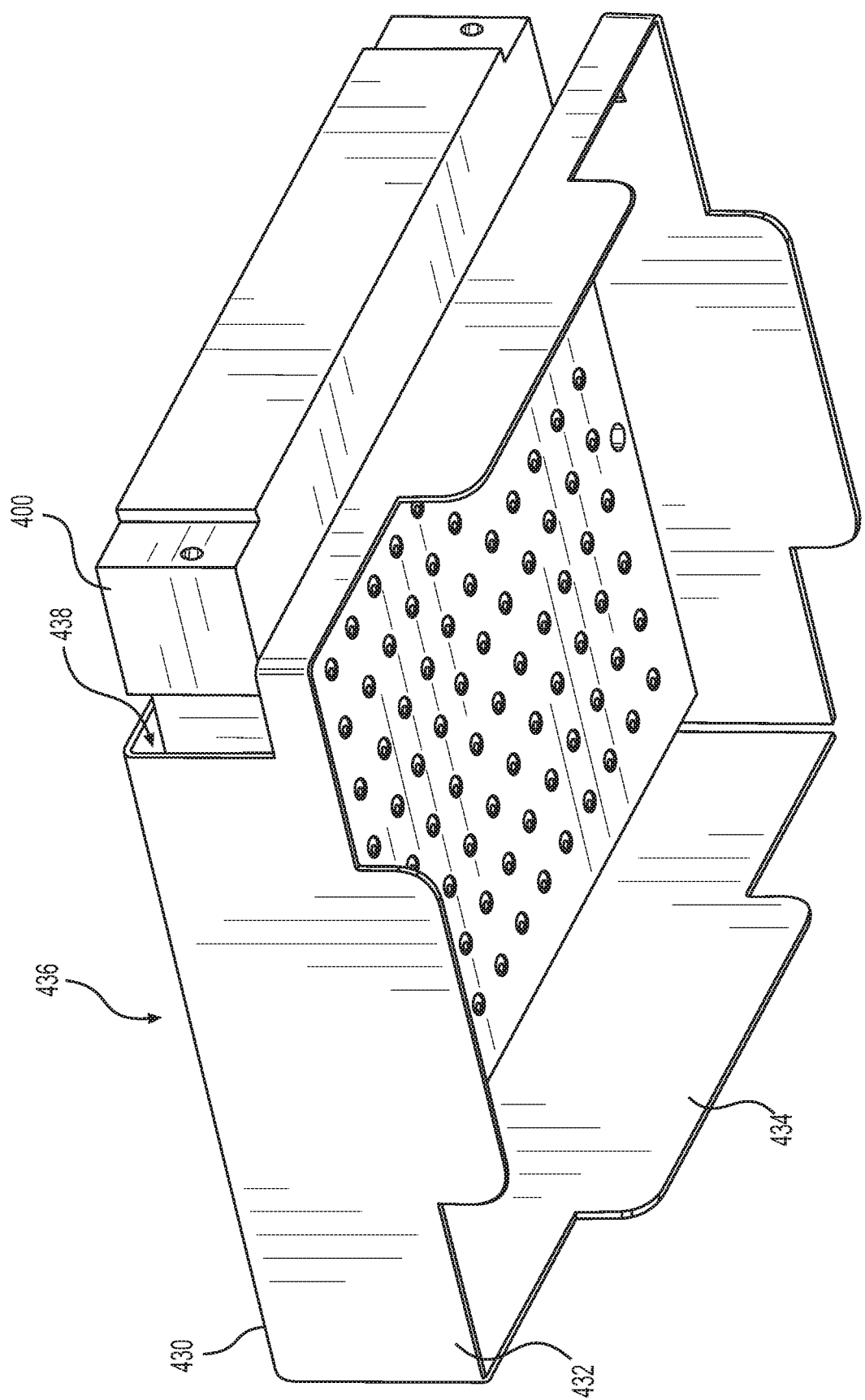

FIG. 20 is a perspective view of an optional splashguard of the present invention.

Figure 21:
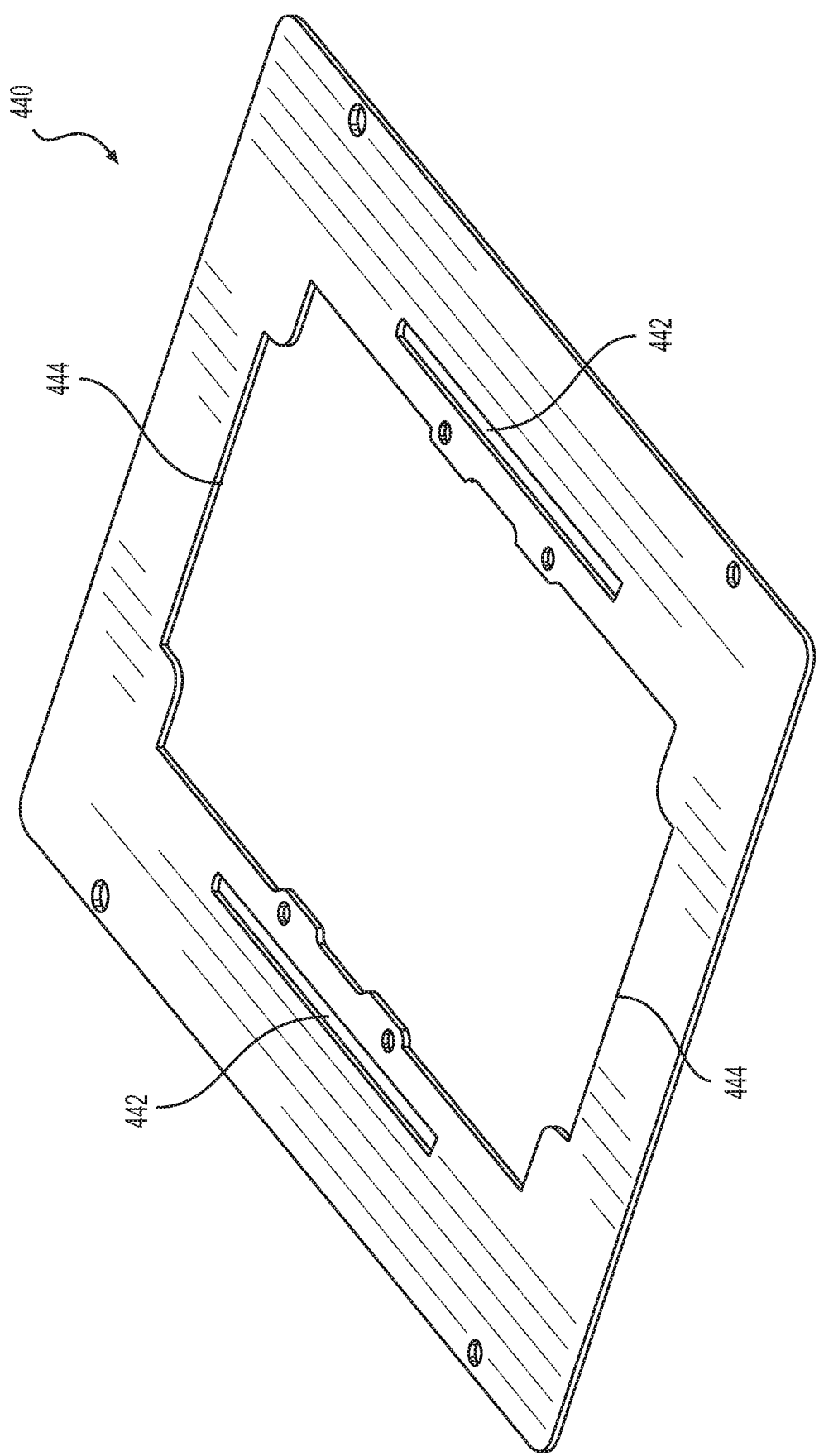

FIG. 21 is a perspective view of an optional tip rack support platform for use with the optional splash guard of FIG. 20.

Figure 22:
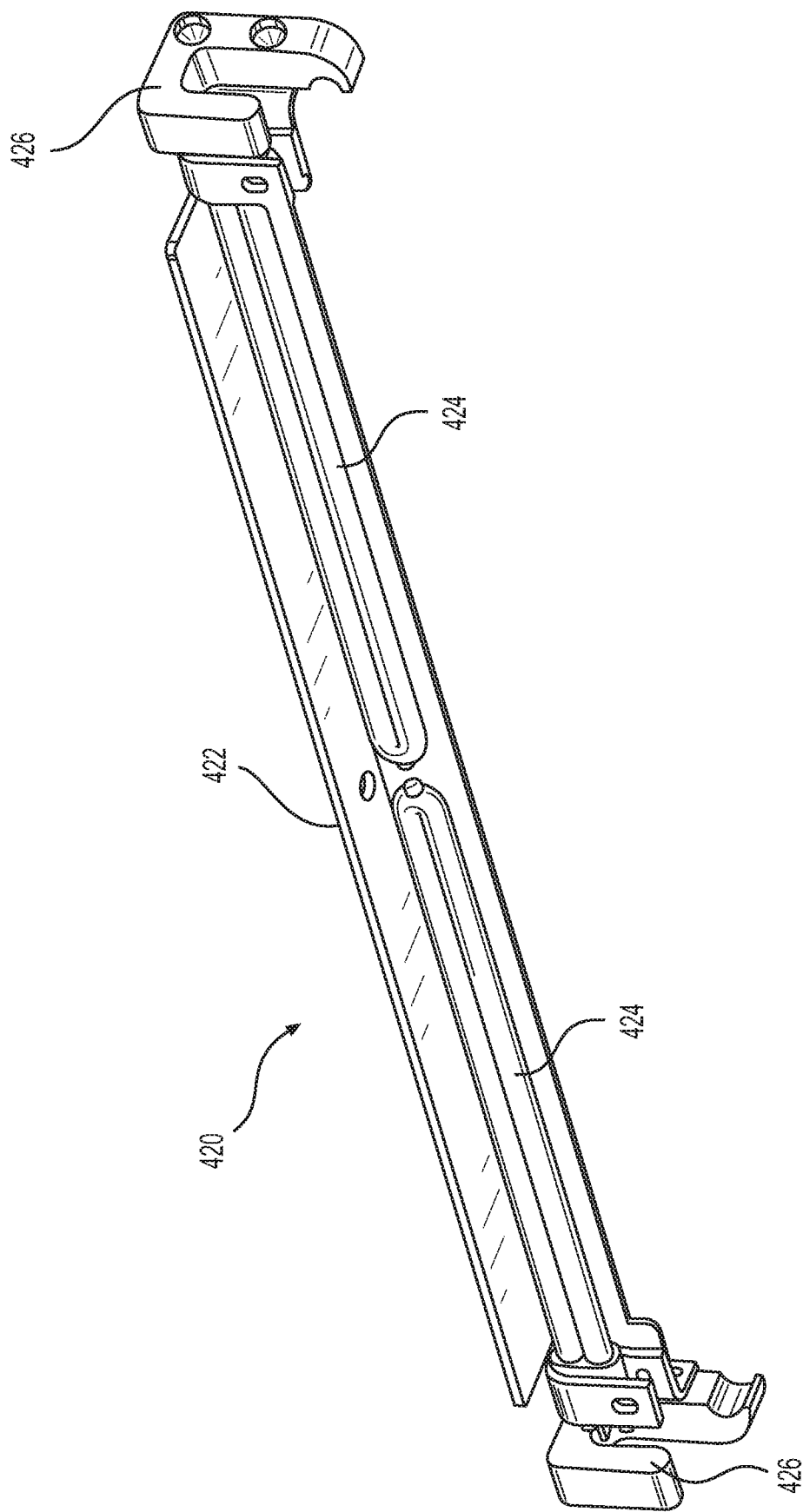

FIG. 22 is a perspective view of a UV curtain of the present invention.

DETAILED DESCRIPTION

An exemplary pipette tip washing device 10 is illustrated in FIGS. 1-3B. The pipette tip washing device 10 includes a top compartment 12, manifold dispensers 14, tip racks 16, a tip rack support 18, a middle compartment 20, a wash sleeve 22, a bottom compartment 24, an ultraviolet (UV) light source 26, and optional transducers 27, although the pipette tip washing device 10 may include other elements in other configurations. This exemplary technology includes a number of advantages including providing a device and method for the efficient and economical sterilization of a large number of pipette tips for use in large scale laboratory settings.

Figure 1A:
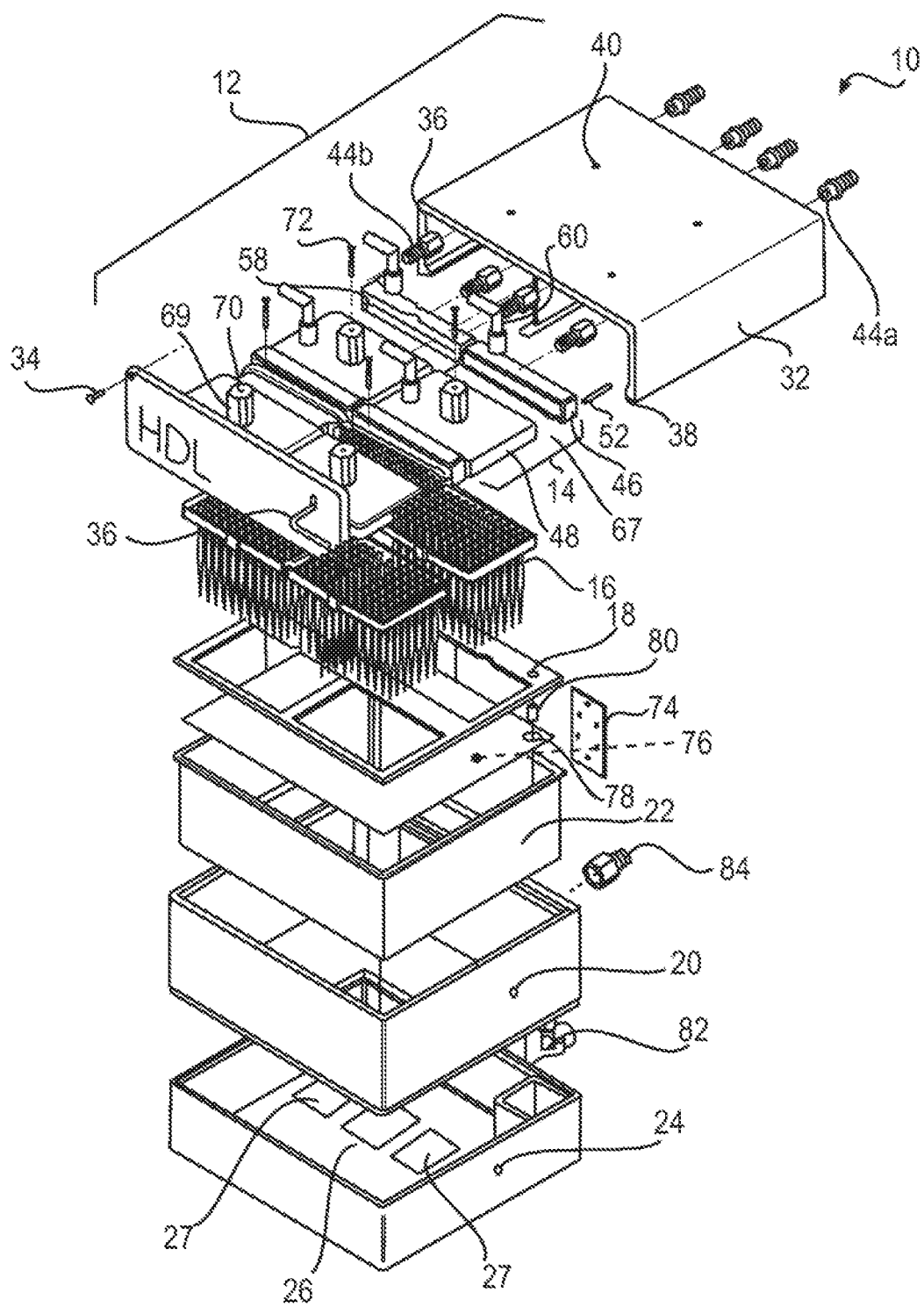
FIGS. 1A and 1B are exploded perspective views of an exemplary embodiment of a pipette tip washing device of the present disclosure.
Figure 1B:
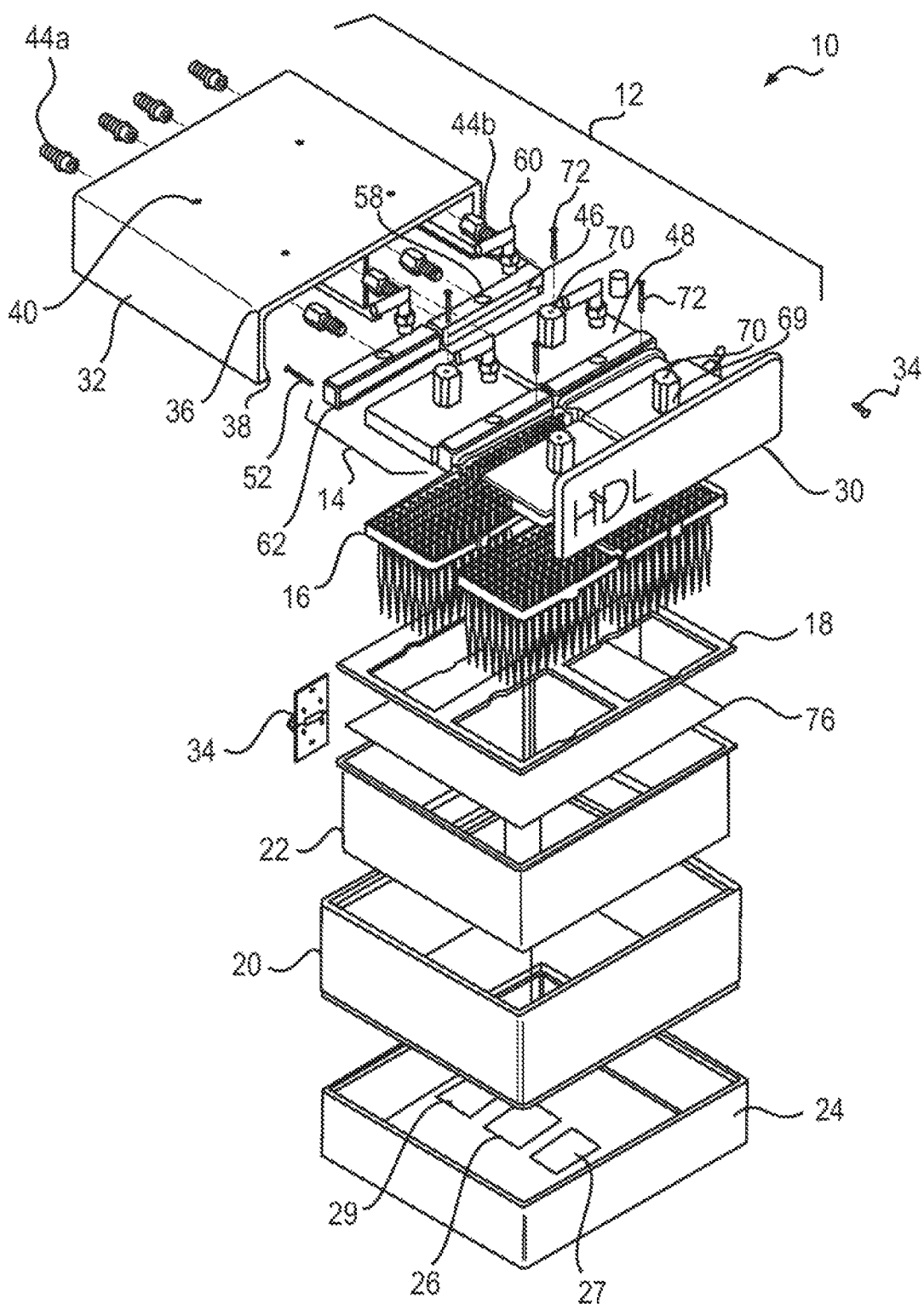
Figure 2:
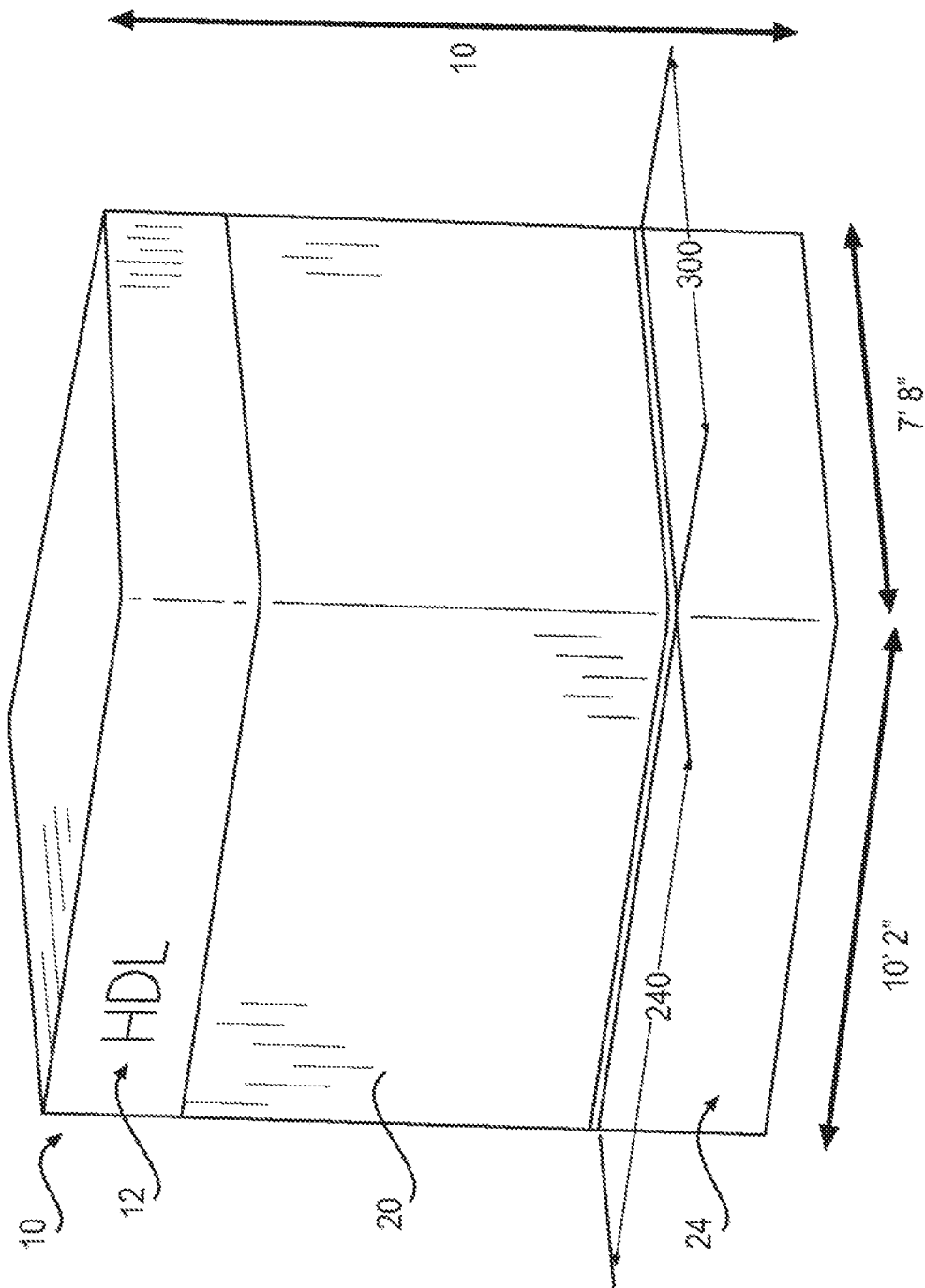
FIG. 2 is a perspective view of the exemplary pipette tip washing device of the present disclosure.
Figure 3A:
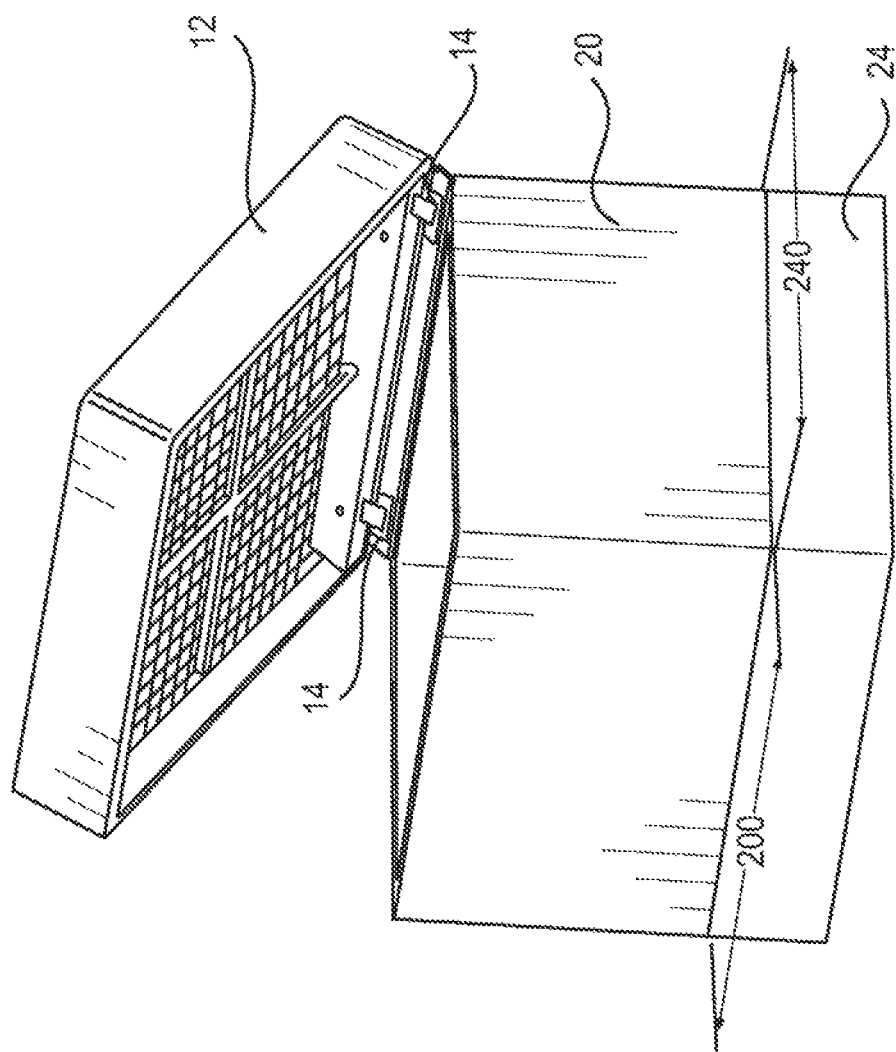
FIGS. 3A and 3B are front and rear perspective views of the exemplary pipette tip washing device of the present disclosure with the top compartment in an open position.
Figure 3B:
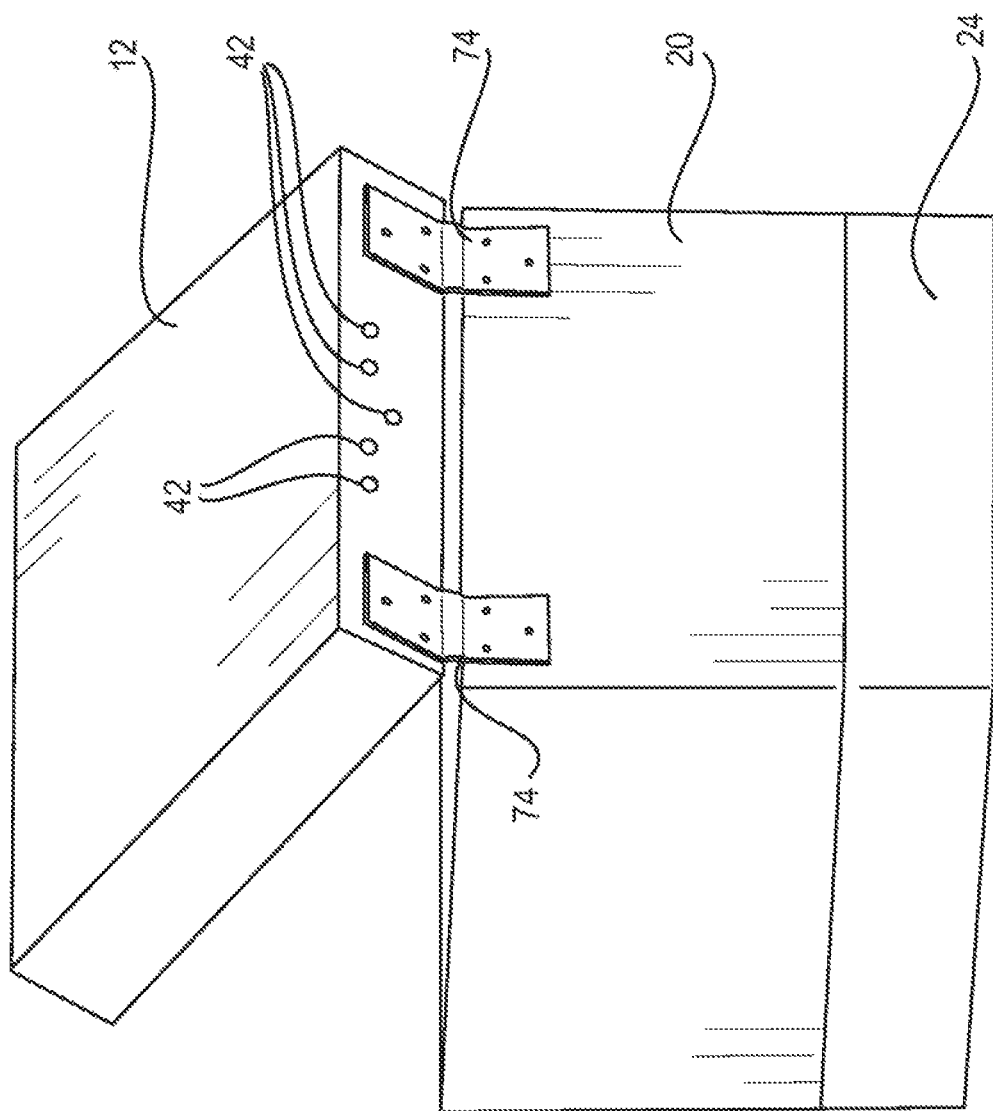
Figure 4A:
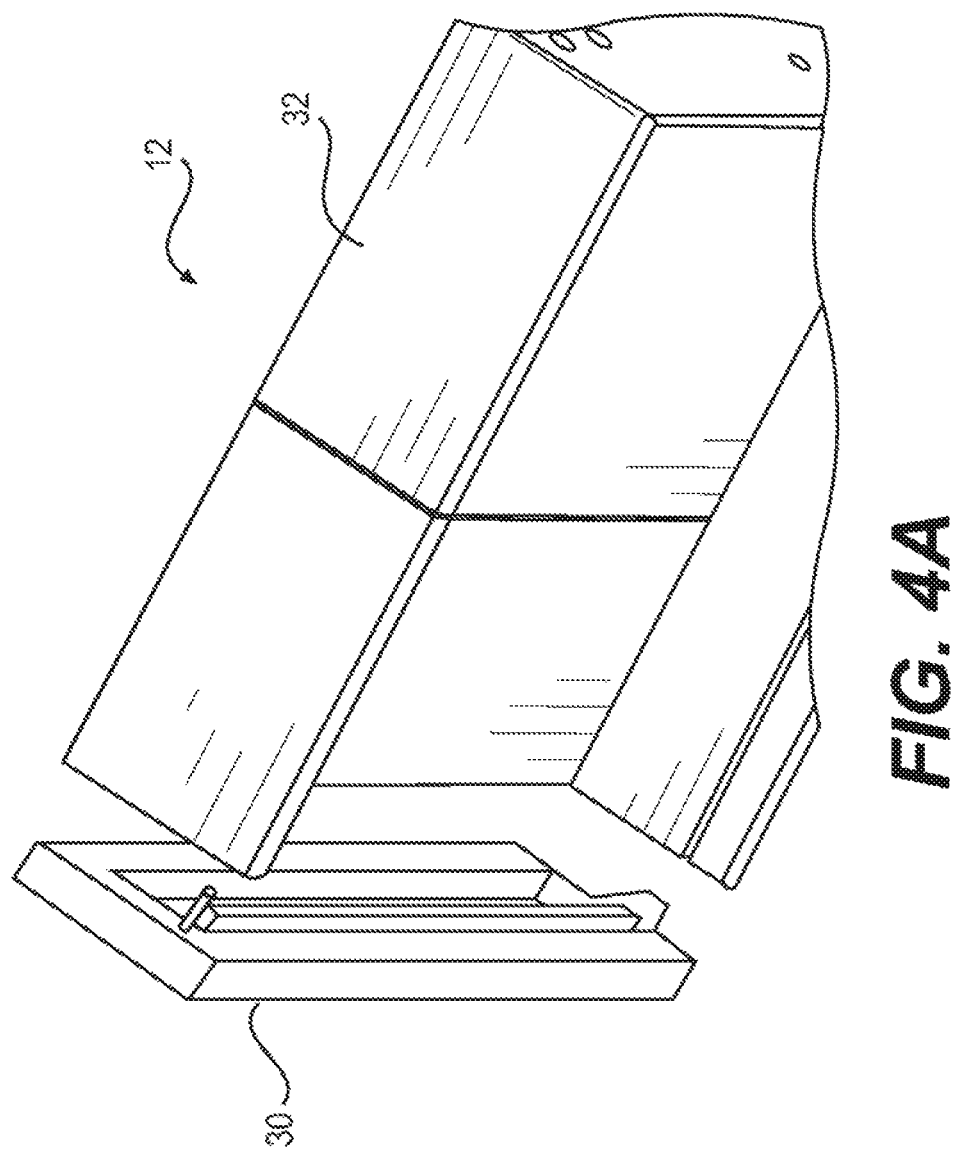
FIG. 4A is a perspective view of a top compartment of the pipette tip washing device illustrated in FIG. 1.
Figure 4B:
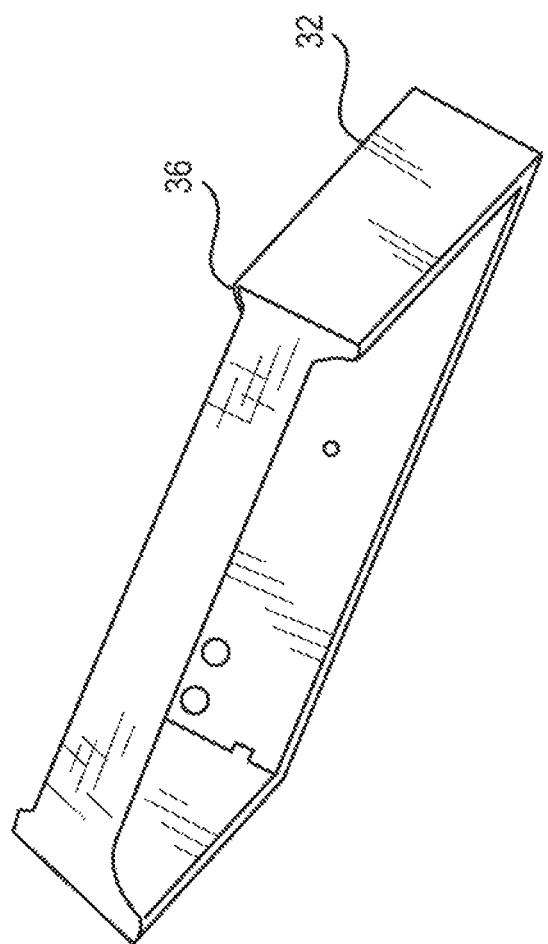
FIG. 4B is a perspective view of a receiving compartment of the top compartment illustrated in FIG. 4A.
Figure 5A:
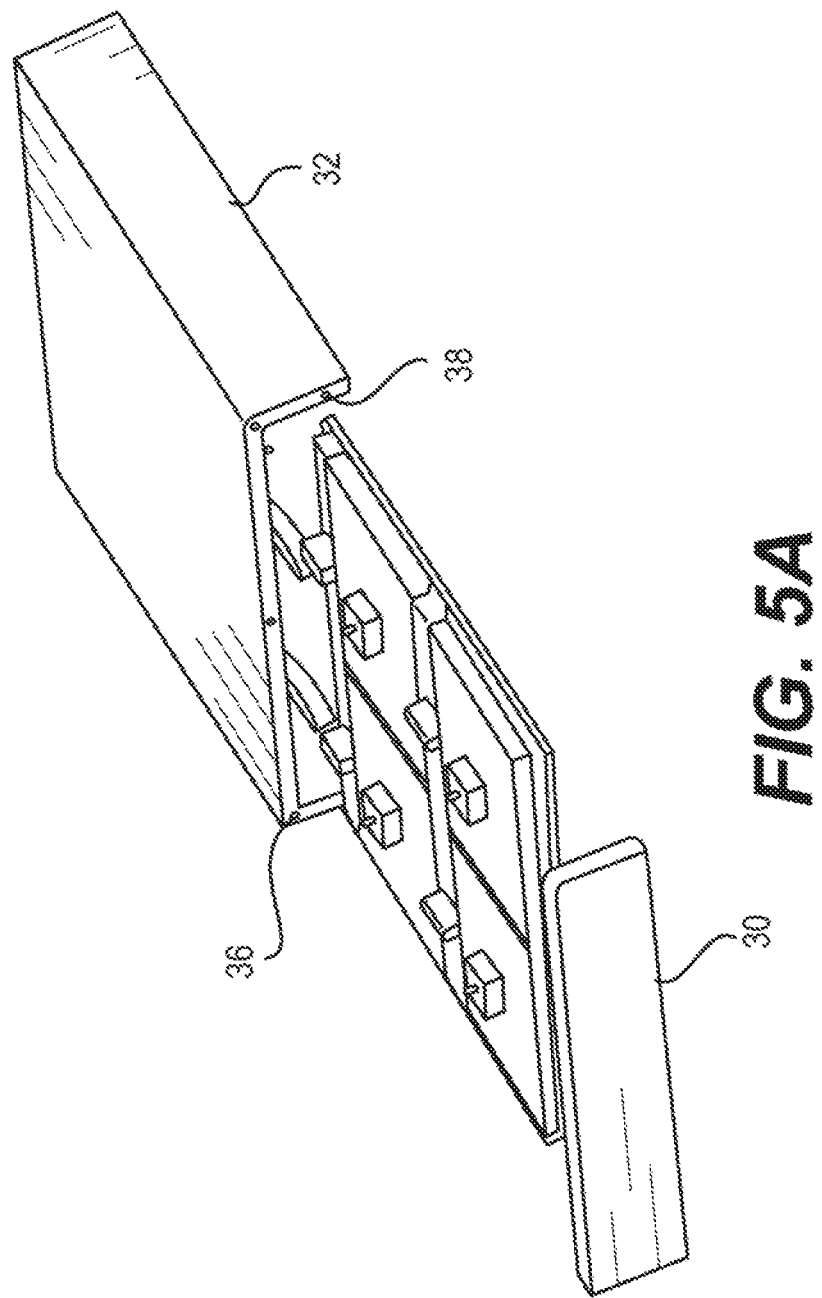
Figure 5B:
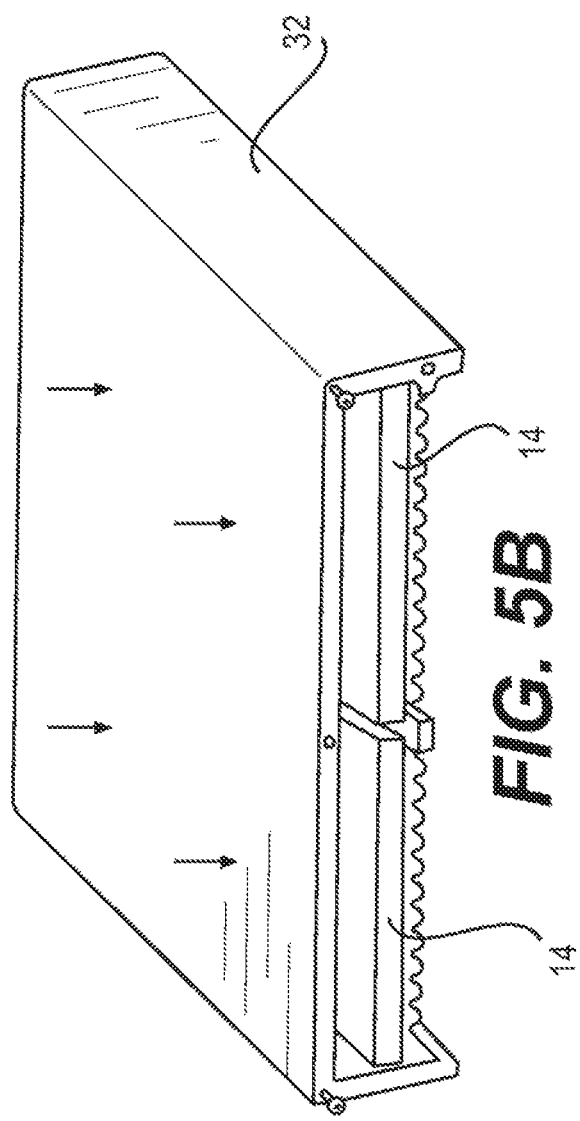
Figure 5C:
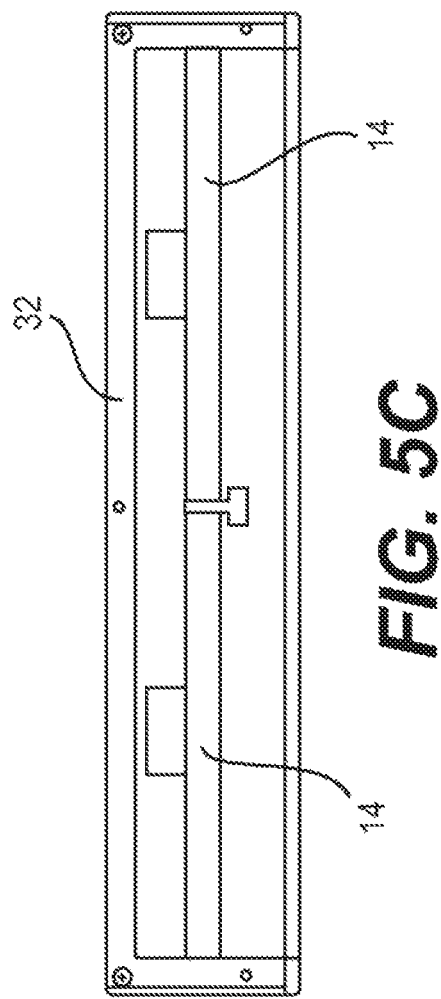

Referring more specifically to FIGS. 4A-4B, an exemplary top compartment 12 of the exemplary pipette tip washing device 10 is shown. The top compartment 12 includes a front cover 30 removably coupled to a receiving chamber 32, although the top compartment 12 may include other elements in other configurations. Front cover 30 is constructed of stainless steel, although front cover may be constructed of other numbers and types of materials. Front cover 30 is removably coupled to the receiving chamber 32 through one or more one or more screws 34 which are inserted into holes 36 in the receiving chamber 32, although other attachment methods may be utilized to removably couple front cover 30 to receiving chamber 32.

Receiving chamber 32 is configured to receive the one or more manifold dispensers 14 as illustrated in FIGS. 5A-5D. In this example, receiving chamber 32 is configured to receive four manifold dispensers 14, although receiving chamber 32 may receive other numbers of manifold dispensers 14 in other configurations. In this example, the receiving chamber 32 includes internal rails 38 on the sidewalls which support the manifold dispensers 14 and one or more holes 40 disposed on the top surface of the receiving chamber 32 configured to receive screws for secure attachment to the manifold dispensers 14, although the receiving chamber 32 may include other elements in other locations to support and securely attach the manifold dispensers 14 within the receiving chamber 32.

Referring again to FIGS. 1A and 1B, the receiving chamber 32 further includes one or more input ports 42 configured to receive liquid input fittings 44a and 44b, which are disposed on opposite sides of the wall of the receiving chamber 32 and are configured to receive liquid into the pipette tip washing device 10 from an external control source (not shown). The external control source may include a pump, control valves, and electronics necessary to deliver wash liquids to the pipette tip washing device 10 in accordance with the present technology. The receiving chamber 32 is constructed of stainless steel, although the receiving chamber 32 may be constructed of other numbers and types materials.

Referring now to FIGS. 6A-6E, an exemplary manifold dispenser 14 is shown. The manifold dispenser is configured to be inserted into receiving compartment 32. The manifold dispenser 14 includes a manifold adapter 46 which may be coupled to a manifold body portion 48, and an O-ring adapter 50, although the manifold dispenser 14 may include other elements in other configurations. In this exemplary manifold dispenser 14, the manifold adapter 46 is coupled to the manifold body portion 48 by screws 52 which are configured to be inserted into the holes 54 and 56 in the manifold adapter 46 and the manifold body portion 48, respectively, although other attachment mechanisms may be utilized. The O-ring adapter 50 is located at the contact point between the manifold adapter 46 and the manifold body portion 48 to provide a watertight seal when the manifold adapter 46 and the manifold body portion 48 are coupled together.

The manifold adapter 46 includes a liquid input 58 configured to receive a manifold elbow input 60 which may be coupled to the liquid input fittings 44b, as illustrated in FIG. 1, to transfer liquid into the manifold adapter 46, although other liquid input ports in other configurations may be utilized to introduce liquid into the manifold adapter 46. The manifold adapter 46 also includes exit ports 62, as illustrated in FIG. 6C, which are coupled to the manifold body portion 48 to transfer liquid from the manifold adapter 46 to the manifold body portion 48. The manifold adapter 46 is constructed of a chemical resistant material such as, by way of example only, polyphenylene sulfide or polyetheretherketone (PEEK), although the manifold adapter 46 may be constructed of other types and numbers of materials.

The manifold body portion 48 includes input ports 64 which are configured to be aligned with the exit ports 62 of the manifold adapter 46 when the manifold adapter 46 and the manifold body portion 48 are coupled. The input ports 64 receive liquid transferred from the manifold adapter 46. The manifold body portion 48 also includes a plurality of liquid outputs 66 configured to operably direct fluid introduced into the manifold dispenser 14 from the manifold body portion 48 into to the wash sleeve 22 to contact a number of laboratory consumables, such as pipette tips. In this example, the liquid outputs 66 are nozzles extending from the manifold body portion 48, although other types of liquid outputs may be utilized in other configurations. The number of liquid outputs 66 in the manifold body portion 48 may match the number of pipette tips in the tip rack 16, which are held below the manifold body portion 48, as illustrated in FIG. 1. By way of example, the manifold body portion 48 may include 96 liquid outputs 66, although manifold body portion 48 may include other numbers of liquid outputs 66 configured for use with different tip racks 16.

Manifold body portion 48 may further optionally include a number of holes 67 in the surface opposite to the liquid outputs 66, the holes 67 being configured to receive fiber optic needles 68. The fiber optic needles 68 extend through the manifold body portion 48 and extend into liquid outputs 66 to direct light into the wash sleeve 22. In one example, the fiber optic needles 68 are attached to the UV-light source 26 to direct UV-light to the wash sleeve 22, although the fiber optic needles 68 may receive light from other light sources in other configurations. The manifold body portion 48 further includes a top support structure 69 including a hole 70 configured to be aligned with hole 40 in the receiving chamber 32. Screw 72 may be inserted through hole 40 in the receiving chamber 32 and hole 70 in the top support structure 68 to securely attach manifold body portion 48 to the receiving chamber 32, although other attachment mechanisms may be utilized. The manifold body portion 48 is constructed of a chemical resistant material such as, by way of example only, polyphenylene sulfide or polyetheretherketone (PEEK), although the manifold body portion 48 may be constructed of other types and numbers of materials.

FIGS. 7A and 7B illustrate another exemplary manifold dispenser 114 that may be utilized with the pipette tip washing device of the present disclosure. Manifold dispenser 114 is the same in structure and operation as the manifold dispenser 14 illustrated in FIGS. 6A-6E, except as illustrated and described herein. Like parts will be described using like reference numerals. The manifold dispenser 114 includes a manifold adapter 146 which may be coupled to a manifold body portion 148, and an O-ring adapter 50, although the manifold dispenser 114 may include other elements in other configurations. In this exemplary manifold dispenser 114, the manifold adapter 146 is coupled to the manifold body portion 148 by screws 52, although other attachment mechanisms may be utilized. The O-ring adapter 50 is located at the contact point between the manifold adapter 146 and the manifold body portion 148 to provide a seal when the manifold adapter 146 and the manifold body portion 148 are coupled together.

The manifold adapter 146 includes a liquid input 58 configured to receive a manifold elbow input 60 which may be coupled to the liquid input fittings 44b, as illustrated in FIG. 1, to transfer liquid into the manifold adapter 146, although other liquid input ports in other configurations may be utilized to introduce liquid into the manifold adapter 146. The manifold adapter 146 also includes a single exit port 162, which is coupled to the manifold body portion 148 to transfer liquid from the manifold adapter 146 to the manifold body portion 148. The manifold adapter 146 is constructed of a chemical resistant material such as, by way of example only, polyphenylene sulfide or polyetheretherketone (PEEK), although the manifold adapter 146 may be constructed of other types and numbers of materials.

The manifold body portion 148 includes an input port 164 which is configured to be aligned with the exit port 162 of the manifold adapter 146 when the manifold adapter 146 and the manifold body portion 148 are coupled. The input port 164 receives liquid transferred from the manifold adapter 146. The manifold body portion 148 also includes a plurality of liquid outputs 66 configured to operably direct fluid introduced into the manifold dispenser 114 from the manifold body portion 148 into to the wash sleeve 22 to contact a number of laboratory consumables, such as pipette tips. In this example, the liquid outputs 66 are nozzles extending from the manifold body portion 148, although other types of liquid outputs may be utilized in other configurations. The number of liquid outputs 66 in the manifold body portion 148 may match the number of pipette tips in the tip rack 16, which are held below the manifold body portion 148, as illustrated in FIG. 1. By way of example, the manifold body portion 148 may include 96 liquid outputs 66, although manifold body portion 148 may include other numbers of liquid outputs 66 configured for use with different tip racks 16.

Manifold body portion 148 may further optionally include a number of holes 67 in the surface opposite to the liquid outputs 66, the holes 67 being configured to receive fiber optic needles 68. The fiber optic needles 68 extend through the manifold body portion 148 and extend into liquid outputs 66 to direct light into the wash sleeve 22. In one example, the fiber optic needles 68 are attached to the UV-light source 26 to direct UV-light to the wash sleeve 22, although the fiber optic needles 68 may receive light from other light sources in other configurations. In this embodiment, the manifold body portion 148 further includes holes 170 configured to receive springs 171. The springs 171 are configured to receive shoulder bolts 172 to attach the manifold body portion 148 to the receiving compartment 32, although other attachment mechanisms may be utilized. The springs 171 allow a range of movement of manifold body portion 148 to provide alignment with the pipette tips prior to washing. The manifold body portion 148 is constructed of a chemical resistant material such as, by way of example only, polyphenylene sulfide or polyetheretherketone (PEEK), although the manifold body portion 48 may be constructed of other types and numbers of materials.

Referring again to FIGS. 1A and 1B, the pipette tip washing device 10 includes four tip racks 16 configured to be inserted into tip rack supports 18, although the pipette tip washing device 10 may include other numbers of tip racks. Although the wash device 10 is described with respect to pipette tips, it is to be understood that the present invention could be utilized with racks which hold other types of laboratory consumables, such as laboratory consumables with similar configurations to pipette tips. Further, the present technology may be utilized with pipette tips of various sizes. By way of example 1, 2, 8, 16 or more tip racks 16 may be utilized for maximization of the throughput in the space available in the receiving compartment 32. In this example, the tip racks 16 hold 96 pipette tips for a total of 384 pipette tips in the pipette tip washing device, although the tip racks 16 may hold other numbers of pipette tips, or other laboratory consumables. The tip rack supports 18 support the tip racks 16 above the wash sleeve 22.

The middle compartment 20 of pipette tip washing device 10 is configured to be attached to the top compartment 12 through hinges 74 such that the top compartment 12 may be lifted in order to insert tip racks 16 into tip rack support 18, although other attachment mechanisms may be utilized to attach the middle compartment 20 to the top compartment 12. The middle compartment 20 is capable of receiving fluid output by the one or more manifold dispensers 14 such that fluid does not enter the bottom compartment 24.

The middle compartment 20 further includes a floor 76 comprising a material transparent to ultraviolet (UV) light, such as by way of example only, quartz, although other transparent materials may be utilized. Floor 76 is configured to provide a water tight-seal that prevents fluid introduced into the middle compartment 20 from entering the bottom compartment 24. Drain 78 exits the floor 76 and directs fluid through drain fitting 80. Drain fitting 80 is coupled to a waste drain elbow fitting 82. The waste drain elbow fitting 82 extends from the drain fitting 80 from the bottom of the middle compartment 20 into the bottom compartment 24 and is coupled to waste output fitting 84 which exits the pipette tip washing device 10 through the bottom compartment 24, although the drain may have other configurations. The middle compartment is further configured to receive the wash sleeve 22. The sidewalls of the middle compartment 20 are constructed of stainless steel, although the middle compartment 20 may be constructed of other numbers and types of materials.

The wash sleeve 22 or wash chamber is configured to be inserted into the middle compartment 20. The wash sleeve 22 is constructed of a material capable of reflecting at least a portion of the UV-light from the UV-light source 26, although the wash sleeve 22 may be constructed of other types and numbers of materials. In another embodiment, the wash sleeve 22 may be constructed of a transparent material, such as quartz by way of example only, in order to direct UV-light into the middle compartment 20 from other light sources, such as the light sources illustrated in FIGS. 8A and 8B below. The wash sleeve 22 is replaceable and protects the sidewalls of the middle compartment 20 from fluid.

The bottom compartment 24 is located below the middle compartment 20 and separated by floor 76. The bottom compartment 24 houses UV-light source 26, such as a UV lamp, which is configured to direct UV-light through the floor 76 into the middle compartment 20, although the UV-light compartment may include other numbers and types of light sources in other configurations. The bottom compartment 24 further may include one or more transducers 27 to direct sound in the ultrasonic range into the middle compartment 20, although other devices may be utilized to direct sound in other ranges to the middle compartment 20. The bottom compartment is easily accessible to replace the UV-light source 26. The bottom compartment 24 is protected from fluids by the floor 76. The bottom compartment 24 further includes an exit port 86 located under drain 78 in floor 76. The drain elbow fitting 82 extends from the drain fitting 80 from the bottom of the middle compartment 20 into the bottom compartment 24 and is coupled to waste output fitting 84 which exits the pipette tip washing device 10 through exit port 86 in the bottom compartment 24, although the drain may have other configurations.

Another embodiment of an exemplary pipette tip washing device 110 is illustrated in FIGS. 8A-9D. Pipette tip washing device 110 is the same in structure and operation as the pipette tip washing device 10 illustrated in FIGS. 1-3B, except as illustrated and described herein. Like parts will be described using like reference numerals. In this embodiment, top compartment 12 is coupled to middle compartment 20 by rails 190 that allow top compartment 12 to be raised vertically along the rails 190 above middle compartment 20. In one embodiment, top compartment 12 is raised in an automated process by mechanical cylinder 192 which is coupled to rod 194, as shown in FIG. 8C, although top compartment 12 may be manually raised.

In this embodiment, middle compartment 20 is disposed on telescopic guides 196 that allow the middle compartment 20 to be opened as a drawer for insertion of tip racks 16, although other devices that allow middle compartment to be opened may be utilized. Middle compartment 20 may be opened and closed in an automated process by cylinder 198, although middle compartment 20 may be opened manually as well. Middle compartment 20 further includes UV light sources 126 disposed on the inside surface thereof. The UV light sources 126 may be utilized with a transparent wash sleeve to direct light onto pipette tips held in pipette tip racks 16 during operating of the pipette tip washing device 110.

In this embodiment, the middle compartment 20 further includes mechanical cylinders 199 that may operatively raise and lower the tip racks 16 when the top compartment 12 is in an open position. The mechanical cylinders 199 may be utilized to agitate the pipette tips to improve wash quality during the wash process or to assist in the drying process.

Figure 9A:
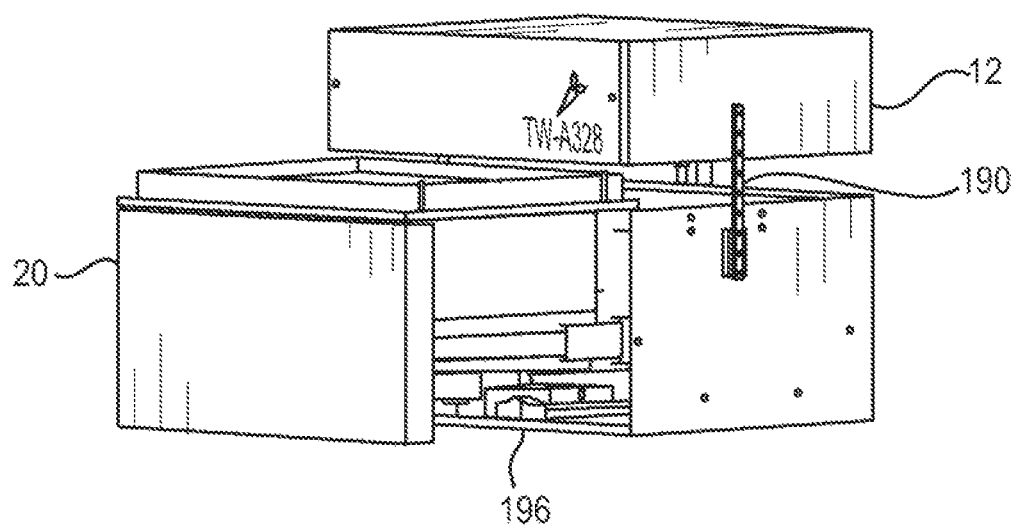
Figure 9B:
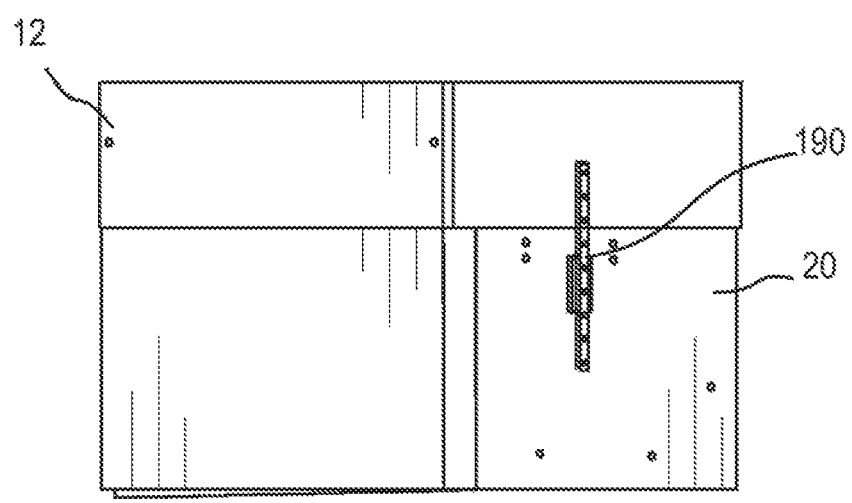
Figure 9D:
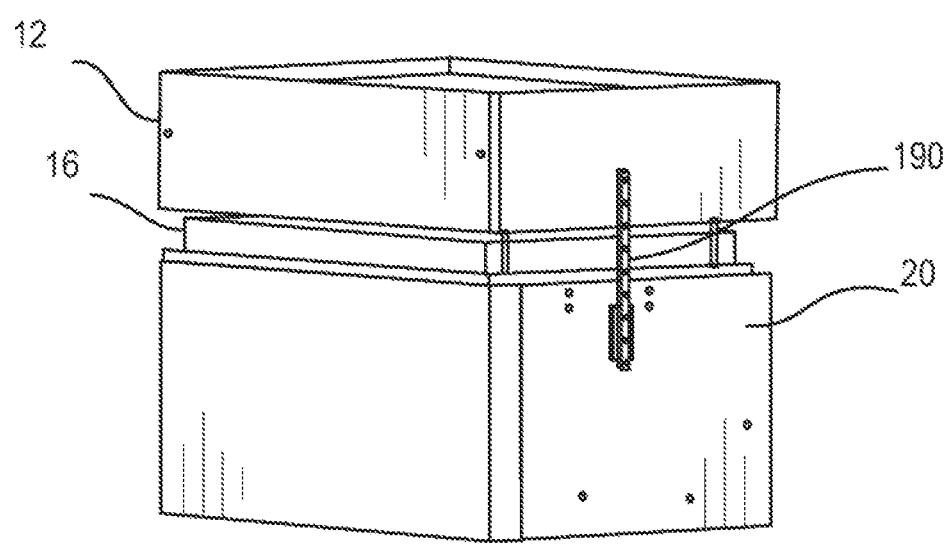

Referring now to FIGS. 9A-9D, the pipette tip washing device 110 is illustrated in various states of operation. FIG. 9A shows the pipette tip washing device 110 in an opened position with top compartment 12 raised and middle compartment 20 opened as a drawer for the insertion of pipette tips. FIG. 9B shows the pipette tip washing device 110 in the closed position for washing the pipette tips. FIGS. 9C and 9D illustrate the movement of the tip racks 16 with the top compartment 12 raised in order to agitate the pipette tips to assist in the drying process.

A method for washing pipette tips using the pipette tip washing device 10 will be described with reference to FIGS. 1-9D. One or more tip racks 16 containing pipette tips are loaded into the pipette washing device 10, although the present method may be utilized for other laboratory consumables. The one or more tip racks 16 are supported in the pipette tip washing device 10 by tip rack support 18. The one or more tip racks 16 may hold 24, 48, 96, 98, 100, 140, 168, 384, or 1536 pipette tips, by way of example, although the one or more tip racks 16 may hold other numbers of pipette tips. The pipette tip washing device 10 may be utilized with pipette tips with volumes of 10 µL-5 mL, such as 10 µL, 50 µL, 1 mL, or 5 mL pipettes, by way of example, with corresponding lengths between 30 mm-120 mm, although the pipette tip washing device 10 may be utilized with pipette tips with other sizes and configurations. Pipette tip washing device 10 may be utilized to clean both conductive and non-conductive pipette tips. Manifold body portions 48 having different numbers of liquid outputs 66 may be interchanged based on the number of pipette tips in the one or more tip racks 16.

One or more liquid washing or rinsing solutions are directed into the pipette tip washing device 10 through input ports 42. The liquid solutions may be pumped into the pipette tip washing device 10 by the pump in the external control source (not shown). In one embodiment, the liquid may be provided in a pressurized flow to assist in the cleaning process. The liquid solutions may be deionized water, bleach, hydrogen peroxide, one or more enzyme solutions, ethanol, detergent, purified water, water, ammonia, isopropanol, alcohol, a solution capable of substantially rinsing or decontaminating plastic, or combinations thereof, although other liquid solutions in other combinations may be utilized. In one example, the following liquid solutions are applied for washing/rinsing prior to draining: a) deionized water, b) deionized water and 5-10% bleach solution, c) deionized water, d) ethanol, although other liquid solutions may be applied in other combinations.

The liquid solutions enter the manifold dispensers 14 through the liquid input 58 in the manifold adapter 46. The liquid solutions are then directed through the manifold body portion 48. The liquid solutions exit the manifold body portion 48 at liquid outputs 66 and enter the middle compartment 20 to contact the pipette tips held in the one or more tip racks 16. The liquid outputs 66 may direct the liquid solution through the pipette tips or may possibly direct the pipette tips to uptake washing fluid for washing/rinsing.

The liquid solutions enter the middle compartment 20. Quartz floor 76 prevents the liquid solution from entering the bottom compartment 24. The liquid solution may exit the pipette washing device 10 through drain 78. In one example, the pipette tips may be submerged in the liquid solutions that are filled on top of the quartz floor 76 prior to being removed from the middle compartment 20 through drain 78.

The liquid solutions are then removed from the pipette washing device 10 through drain 78. In one example, 4 cycles of liquid solutions (water rinse, soap rinse, etc.) are directed into the middle compartment 20 prior to draining the fluids. After draining the liquid solutions, the pipette tips are at least substantially dried, although the pipette tips may be completely dried. In one example, the pipette tips are substantially dried by agitating the pipette tips, although other drying mechanisms may be utilized to substantially dry the pipette tips.

Throughout the wash process, the UV light source 26, by way of example, is engaged to expose the outer surfaces of the pipettes to ultraviolet light to sterilize the pipettes. The UV light source 26 directs light to the pipettes through the quartz floor 76, although UV light may be directed from other directions from other UV light sources, such as light sources 126 as illustrated in FIGS. 8A and 8B. The UV light source 26 may further direct light through the fiber optic needles 68 located in the openings of the liquid outputs 66 in the manifold body portion 48. The fiber optic needles 66 direct UV light to the inside of the pipette tips to provide sterilization of the interior surfaces of the pipette tips. Additionally, the pipette tips may be exposed to sound in an ultrasonic range from the one or more transducers 27, which direct the sound in the ultrasonic range into the washing chamber.

It may be difficult if not impossible to locate a pump that is strong enough to pump the cleaning fluid(s) from the cleaning fluid source, through all of the supply tubing, through the manifold(s), and out of the output holes (in one embodiment of the invention, the length of the overall tubing that the liquid gets pumped into is 27 inches and the inner diameter of the tubing is 0.5 inch, there are four manifolds, and 96 output holes) at a sufficiently high pressure to clean the objects to be cleaned, while also being small enough to fit into a desired overall small footprint of the washing device. Embodiments of the invention use a novel approach of alternatingly pumping cleaning fluid into the supply lines and manifold and flowing compressed air through the supply lines and manifold, such that the compressed air drives the cleaning fluid out through the output holes at a higher pressure than would be possible using the fluid pump alone.

Referring now to FIG. 10, a block diagram of a liquid and air supply portion of embodiments of the present invention is illustrated. In the illustrated embodiment, the washing device comprises a liquid dispenser 212 that operably directs a cleaning fluid to contact one or more objects to be cleaned (such as pipettes as described above). The liquid dispenser may comprise one or more manifold dispensers, as described above, one or more liquid dividers or distributors, or any other suitable liquid dispensing mechanism. A dispensing line 220 directs the cleaning fluid to the fluid dispenser 212. (The fluid dispenser typically has an internal volume (i.e., is not just an outlet port or ports) that contains some of the cleaning fluid during operation. In this regard, the dispensing line and fluid dispenser may together be considered a reservoir of cleaning fluid.) The cleaning fluid is supplied to the liquid dispenser 212 from one or more liquid sources 200. More than one cleaning fluid may be used (e.g., cleaner, rinse agent, disinfectant, etc.) (the term "cleaning fluid" is used generically herein to refer to any fluid or combination of fluids used in the cleaning process), separately or in combination, but the use of only one will be described in relation to FIG. 10 for simplicity. The liquid source 200 may comprise a container or reservoir, a fixed supply line, or any other suitable mechanism for storing and/or supplying the cleaning fluid. (The liquid source may be considered to at least partly comprise the fluid supply line leading from the liquid source.) Pump 202 (which may be mechanical, electrical, pneumatic, etc.) selectively pumps the cleaning fluid from the liquid source 200 into a fluid supply line 218, which is connected via T-fitting 210 to the dispensing line 220. A one-way valve 204 (which may be mechanical, electrical, pneumatic, etc.) downstream from the pump 202 prevents the cleaning fluid from flowing upstream toward the pump 202 when compressed air is supplied to the dispensing line 220 (described below).

A compressed air source 206 selectively supplies compressed air to the dispensing line 220 via an air supply line 216. Air supply line 216 is connected via T-fitting 210 to the dispensing line 220. An air valve 208 (which may be mechanical, electrical, pneumatic, etc.) selectively allows or prevents the flow of air from the compressed air source 206. Compressed air source 206 may comprise any suitable source of compressed air, such as an air cylinder, an air compressor, or a fixed air supply line.

A controller 214 (or multiple controllers) is configured to alternatingly activate (a) the pump 202 to pump the cleaning fluid from the liquid source 200 into the dispensing line and (b) the air valve 208 to force the cleaning fluid from the dispensing line 220 out through the liquid dispenser 212. Typically, the pump is activated at least until the dispensing line 220 and liquid dispenser 212 are filled with the cleaning fluid, and the air valve is activated at least until substantially all of the cleaning fluid in the dispensing line 220 and liquid dispenser 212 is forced from the dispensing line via outlets on the liquid dispenser 212. In this regard, the cleaning fluid pumped into the dispensing line and liquid dispenser is expelled at high pressure by the supply of compressed air.

In operation, air valve 208 is off/closed, and pump 202 is turned on (for about 1-5 seconds in one embodiment of the invention) to pump cleaning fluid into the dispensing line and liquid dispenser from liquid source 200 until the dispensing line and liquid dispenser are filled with cleaning fluid. The pump 202 is turned off, and the air valve 208 is opened to allow compressed air to flow from the compressed air source 206. One way valve 204 prevents cleaning fluid flowing back toward the pump 202, such that the compressed air forces the cleaning fluid through the dispensing line and out of the liquid dispenser. When substantially all of the cleaning fluid has been forced out, the air valve 208 is closed and the process is repeated until the cleaning cycle is complete.

Any suitable method may be used for determining the necessary duration of the activation of the pump and/or the air valve. The duration of the activation of the pump may be determined by calculating how long it will generally take to fill the dispensing line and liquid dispenser with the cleaning fluid, based on the pump rate and the volume of cleaning fluid that can be held by the dispensing line and liquid dispenser. Alternatively, the duration of the activation of the pump may be determined by using one or more sensors to detect the cleaning fluid in one or more locations in the dispensing line and liquid dispenser.

In one embodiment of the invention, the pump 202 pumps at a rate of about 3-5 liters/minute and the compressed air is supplied at a pressure of about 70 psi.

The controller may comprise a microprocessor, dedicated or general purpose circuitry (such as an application-specific integrated circuit or a field-programmable gate array), a suitably programmed computing device, or any other suitable means for controlling the operation of the pump and air valve (the controller may also control various other components of the washing device to control overall operation of the washing device).

The above-described approach of alternatingly pumping fluid into supply lines or pipes and flowing compressed air through the lines, such that the compressed air drives the fluid out through the output holes at a higher pressure than would be possible using the fluid pump alone, may be used for other devices and purposes other than the above-described washing device, and may be used to dispense other types of fluids and semi-fluids. The above-described approach and systems for accomplishing this approach are within the scope of this patent application, regardless of the specific application. Embodiments of the invention are intended to include such systems and methods. As non-limiting examples, the above-described approach may be used for liquid handling devices in a laboratory for dispensing fluid or semifluid compounds. Additionally, the above-described approach may be used in the food dispensing/packaging industry, such as for dispensing jams or other fluid, semifluid, or semisolid foods into bottles, jars, or other types of packaging.

In this regard, embodiments of the invention may comprise a fluid or semi-fluid dispensing system that may comprise a fluid dispenser for outputting a fluid or semi-fluid, a fluid source, a dispensing line directing the fluid or semi-fluid from the fluid source to the fluid dispenser, a compressed air source, an air valve selectively controlling a flow of air from the compressed air source into the dispensing line, a pump selectively pumping the fluid or semi-fluid from the fluid source into the dispensing line, and a controller for alternatingly activating the pump to pump the fluid or semi-fluid from the fluid source into the dispensing line and the air valve to force the fluid or semi-fluid from the dispensing line via the fluid dispenser. Such a fluid or semi-fluid dispensing system is similar to the liquid and air supply portion of the washing device illustrated in FIG. 10, however such a fluid or semi-fluid dispensing system is not limited to use in a washing device.

The fluid dispenser may comprise a simple fluid outlet or opening, a nozzle, a spray nozzle, or the like. Alternatively, the fluid dispenser may comprise a more complex fluid distribution device such as the above-described manifold dispenser.

The fluid pump may comprise any suitable pumping device, of any suitable size or pumping capacity. The fluid dispensing system of embodiments of the invention is not limited to systems in which the fluid pump is not able strong enough to pump the fluid or semi-fluid from the fluid source, through all of the supply tubing, and out of the fluid outlet.

However, the fluid dispensing system of embodiments of the invention is particularly advantageous in such situations.

As described above, the process of alternatingly activating (a) the pump to pump the fluid or semi-fluid from the fluid source into the dispensing line and (b) the air valve to force the fluid or semi-fluid from the dispensing line via the fluid dispenser is repeated as needed (at least twice, but more typically many times) for whatever process is being performed.

Another embodiment of an exemplary pipette tip washing device 310 is illustrated in FIGS. 11-17. Pipette tip washing device 310 is similar in structure and operation as the pipette tip washing device 110 illustrated in FIGS. 8A-9D. However, in this embodiment, top compartment is not raised and lowered vertically to alternate between loading/unloading and washing positions (which indirectly raised and lowered the manifold dispensers). (Minor vertical adjustments, as well as side-to-side and front-to-back adjustments, may be made to the top compartment, as described below.) Rather, the manifold dispensers are raised and lowered vertically within the top compartment (while the top compartment remains still) to alternate between loading/unloading and washing positions, as described below.

Referring now to FIGS. 11-14, the pipette tip washing device 310 is illustrated in various states of operation. FIGS. 11 and 13 show the pipette tip washing device 310 in a closed or washing position for washing the pipette tips. FIG. 12 shows the pipette tip washing device 310 in an open or loading/unloading position, with the drawer compartment 320 (which may also be termed the middle compartment) opened for the insertion of pipette tips. The outer skin is removed in FIGS. 12-14 for visibility of the internal components. Additionally, some of the internal walls have been removed in FIG. 14 for improved visibility of internal components. The air lines and most of the fluid lines are omitted for clarity.

The pipette tip washing device 310 has an outer shell 312 to conceal the internal components for safety and aesthetics. The pipette tip washing device 310 comprises a top compartment 314 and a drawer compartment (or middle compartment) 320. The pipette tip washing device 310 may also comprise a bottom compartment 326. The drawer compartment 320 is selectively movable out and in between, respectively, an open or loading/unloading position (shown in FIG. 12) and a closed or washing position (shown in FIGS. 11 and 13). The drawer compartment is capable of receiving a plurality of laboratory consumables (such as pipette tips) held by one or more racks (the pipette tip washing device 310 as illustrated holds four such racks). The top compartment 314 is positioned above the drawer compartment 320 when the drawer compartment is in its closed position (FIGS. 11 and 13). The bottom compartment 326 (when present) is positioned below the drawer compartment 320 when the drawer compartment is in its closed position (FIGS. 11 and 13).

The drawer compartment 320 is opened to load laboratory consumables to be washed and to unload laboratory consumables that have been washed. The drawer compartment 320 is closed to wash the loaded laboratory consumables.

Within the top compartment is an inner wall 332 that has a horizontal center section and opposing vertical side walls. The inner wall 332 provides support and mounting surfaces for various components (e.g., manifold dispensers, UV curtain, etc.), discussed further below. Within the outer shell 312 and forming part of both the drawer (or middle) compartment and the bottom compartment is an inner wall 330 that has a back wall, opposing side walls, and an open front.

The inner wall 330 provides support and mounting surfaces for various components (e.g., UV light, agitation cylinders, etc.), discussed further below. The inner wall 332 is affixed to and held above the inner wall 330 via opposing support members 334. As seen in FIGS. 12 and 13, the support members 334 have elongated horizontal slots to enable front-to-back adjustment of the position of inner wall 332 relative to inner wall 330. Similarly, the support members 334 have elongated vertical slots to enable up-and-down adjustment of the position of inner wall 332 relative to inner wall 330. Inner wall 332 has elongated slots 336 to enable side-to-side adjustment of the position of the horizontal center section of inner wall 332 to its opposing vertical side walls. The adjustability provided by the slots on the support members 334 and the slots 336 on the inner wall 332 enable adjustment of the positions of the manifold dispensers relative to the laboratory consumables when the drawer compartment is closed to ensure proper alignment of the liquid outputs with the laboratory consumables during operation.

The drawer compartment 320 comprises a washing chamber 380 that is capable of receiving and retaining fluid output by the liquid outputs of the manifold dispensers. The washing chamber 380 comprises four walls, a floor, and an open top. A waste drain (not illustrated) dispenses the retained liquid from the washing chamber 380. The drawer compartment 320 is disposed on telescopic guides 382 that allow the drawer compartment 320 to be opened as a drawer for loading and unloading the laboratory consumables. The drawer compartment 320 is typically opened and closed in an automated process initiated by pressing an OPEN/CLOSE button or the like on a user interface (not illustrated).

The floor of the washing chamber 380 may be constructed of Quartz glass. A UV light source (not illustrated) may be positioned in the bottom compartment 326 below the washing chamber (when the drawer compartment is closed). The Quartz floor the washing chamber allows UV light to pass through and reach the laboratory consumables. In addition, the inner surfaces of the walls of the washing chamber may be constructed of polished stainless steel, which enables the UV light to bounce off of the walls and reach all sections of each laboratory consumable during operation of the pipette tip washing device 310.

As seen in FIG. 17, the drawer compartment comprises a substantially horizontal top surface or platform 384 at the open top end of the washing chamber 380. The top surface 384 defines openings for receiving racks holding laboratory consumables. In the illustrated embodiment, two opening are defined with each opening receiving two racks. The openings in the top surface are sized such that most of the racks extend down into the washing chamber. Pairs of opposing clips 388 are used to grasp and hold opposing sides of each rack. The clips 388 engage ridges on opposing sides of the racks.

Some racks for holding laboratory consumables may not have the necessary structure to be grasped and held by the clips 388. However, such racks may have a shoulder surrounding the top edge of the rack that enables the rack to sit suspended in an opening that is sized such that the shoulder engages the edge of the opening. To enable the pipette tip washing device 310 to wash items held by either type of rack, a tip rack adapter 386 (seen in FIG. 12) is selectively mountable to the top surface 384. The adapter 386 defines four openings that are smaller than the openings defined by the top surface 384. Each opening defined by tip rack adapter 386 is sized to enable a rack to sit suspended in the opening. As above, most of the racks extend down into the washing chamber (although possibly less than if the clips 388 are used). The tip rack adapter 386 may be selectively affixed to the top surface 384 using any suitable mechanism that is secure yet readily affixable/removable.

The top surface or platform 384 may be movable relative to the washing chamber 380. In this regard, the top surface 384 may be selectively agitatable. Agitating the top surface 384 in turn agitates the tip racks and the laboratory consumables in the racks to improve wash quality during the wash process and/or to assist in the drying process by removing excess liquid. The pipette tip washing device 310 may comprise one or more cylinders 392 (which may be, for example, pneumatic or hydraulic cylinders) for selectively agitating the platform. The cylinders are typically affixed to the inside surface of inner wall 330 and positioned such that the cylinders are below the top surface 384 when the drawer compartment 320 is in its closed position. The cylinders are typically positioned with their cylinder rods projecting upward. Extending the cylinder rod causes the cylinder rod to contact the underside of the top surface 384 and lift a portion of the top surface 384 away from the washing chamber 380, while retracting the cylinder rod causes the portion of the top surface 384 to lower back down to the washing chamber 380. Rapidly extending and retracting the cylinder rods multiple times provides the desired agitation. If more than one cylinder is used, the cylinders may operate synchronously or asynchronously. In alternative embodiments of the invention, the agitating cylinders may be positioned above the platform (or in any other suitable location). In such an alternative embodiment, the cylinder rods would likely be affixed to the platform in some way to enable the extension and retraction of the cylinder rods to move the platform to provide the desired agitation.

The drawer compartment 320 of the pipette tip washing device 310 comprises a splashguard 390 projecting upward to help keep liquids from splashing out of the device during operation.

The top compartment 314 houses one or more manifold dispensers 340 (four are illustrated). The manifold dispensers 340 of the pipette tip washing device 310 typically (although not necessarily) have a similar structure as described above in relation to other embodiments of the pipette tip washing device. FIG. 18 illustrates one embodiment of a manifold dispenser that may be used with the pipette tip washing device 310. Each manifold dispenser 340 of FIG. 18 comprises a manifold adapter 344 coupled to a manifold body portion 342. Each manifold dispenser 340 comprises at least one liquid input (to which are attached fitting 346, which are visible in FIGS. 15 and 16) and a plurality of liquid outputs 348 that operably direct fluid to contact the plurality of laboratory consumables held by the rack when the manifold dispenser is in its washing position and the drawer compartment is in its closed position. In the case of the manifold dispenser 340 of FIG. 18, each of the plurality of liquid outputs 348 comprises a nozzle that projects downward from the manifold body portion 342. Each nozzle is encircled by a washer 350, O-ring, or the like. When the manifold dispenser is in its washing position, the washers 350 contact the tops of corresponding ones of the laboratory consumables. This contact helps ensure that the cleaning fluids are directed down into the laboratory consumables.

FIG. 19 illustrates an alternative embodiment of a manifold dispenser that may be used with the pipette tip washing device 310. Each manifold dispenser 400 of FIG. 19 comprises a manifold adapter 404 coupled to a manifold body portion 402. Each manifold dispenser 400 comprises at least one liquid input (to which are attached a fitting similar to fitting 346 of manifold dispenser 340 visible in FIGS. 15 and 16) and a plurality of liquid outputs that operably direct fluid to contact the plurality of laboratory consumables held by the rack when the manifold dispenser is in its washing position and the drawer compartment is in its closed position. In the case of the manifold dispenser 400 of FIG. 19, a flexible mat 408 (constructed of, for example, silicone) is affixed to the bottom surface of the manifold body portion 402. The mat 408 has a plurality of through-holes 410 defined therein. Each of the through-holes 410 is aligned with a corresponding output hole 412 in the bottom surface of the manifold body portion 402. Thus, each output hole 412 in the bottom surface of the manifold body portion and corresponding aligned through-hole 410 in the mat 408 may be considered together to form each of the plurality of liquid outputs. When the manifold dispenser is in its washing position, the mat 408 contacts the tops of all of the laboratory consumables, with one or more of the through-holes 410 aligned with a corresponding one of the laboratory consumables. This contact helps ensure that the cleaning fluids are directed down into the laboratory consumables.

The number of liquid outputs that each manifold dispenser has may be equal to the number of laboratory consumables to be washed (per manifold dispenser). For example, manifold dispenser 340 has 96 liquid outputs, and may be used to wash 96 pipette tips held by a rack. As such, each liquid output operably directs washing fluid at one pipette tip. Alternatively, the number of liquid outputs may be a multiple of a number of laboratory consumables to be washed (per manifold dispenser). For example, a manifold dispenser (not illustrated) may have 384 liquid outputs. If such an alternative manifold dispenser is used to wash 96 pipette tips held by a rack, then four liquid outputs would operably direct washing fluid at each pipette tip.

Advantageously, a manifold dispenser with a fixed number of liquid outputs may be able to wash different numbers of laboratory consumables. For example, a manifold dispenser that has 384 liquid outputs may be used to wash 96 pipette tips held by a rack, such that four liquid outputs would operably direct washing fluid at each pipette tip. That same manifold dispenser that has 384 liquid outputs may be used to wash 384 pipette tips held by a rack, such that each liquid output would operably direct washing fluid at one pipette tip. The 384 pipette tips would typically be much smaller such that they fit into the same size rack as the 96 pipette tips.

As mentioned above, the manifold dispensers of the pipette tip washing device 310 are raised and lowered vertically within the top compartment (while the top compartment remains still) to alternate between loading/unloading and washing positions. Any suitable mechanism may be used for raising and lowering the manifold dispensers. Referring now to FIGS. 15 and 16, one possible mechanism for raising and lowering the manifold dispensers is illustrated. FIGS. 15 and 16 are perspective views of two of the manifold dispensers removed from the pipette tip washing device illustrated in FIGS. 11-14. The manifold dispensers are illustrated raised (retracted) in FIG. 15 for loading and unloading the laboratory consumables to/from the tip washer and lowered (extended) in FIG. 16 for washing the laboratory consumables. The mechanism for raising and lowering the manifold dispensers in the illustrated embodiment comprises a manifold support beam 354 and cylinders 356. Two manifold dispensers are supported by each manifold support beam, so two manifold support beams 354 are used in the illustrated embodiment of the tip washer to support the four manifold dispensers 340. The manifold support beams 354 are affixed to the underside of the inner horizontal wall 332, substantially parallel to each other and to the front edge of inner wall 332, and positioned such that the manifold dispensers are positioned in proper relation to the laboratory consumables to be washed when the drawer compartment is closed. Four cylinders 356 (which may be, for example, pneumatic or hydraulic cylinders) are affixed to each manifold support beam 354 such that the cylinder rod projects downward. One manifold dispenser 340 is affixed to two cylinders 356 via braces 360. As such, two cylinders 356 are operated in tandem to raise and lower each manifold dispenser 340. In the illustrated embodiment, cylinders 356 comprise pneumatic double-acting cylinders. As such, cylinders 356 each have two air ports 358.

As seen in FIGS. 12-17 (and particularly in FIG. 14), attached to each liquid input of each manifold dispenser (via a fitting such as fitting 346) is a manifold fluid supply line 370. In the pipette tip washing device 310, there are four such manifold fluid supply lines 370 as there are four manifold dispensers 340. The manifold fluid supply lines 370 extend upward through corresponding holes in the inner wall 332 and connect at their top end to a fluid distribution box 368. In this regard, the manifold fluid supply lines 370 and the fluid distribution box 368 move up and down with the up and down movement of the manifold dispensers. FIGS. 12 and 13 illustrate the movement of the manifold fluid supply lines 370 and the fluid distribution box 368 between, respectively, an up or retracted position for opening and closing the drawer compartment 320 and loading/unloading the pipette tips, and a down or extended position for washing the laboratory consumables. Because the manifold fluid supply lines 370 move up and down with the movement of the manifold dispensers, at least the portion of the manifold fluid supply lines 370 that extends through the holes in the inner wall 332 should be substantially straight and vertical to prevent any undesirable contact between the manifold fluid supply lines 370 and the inner wall 332 as the manifold fluid supply lines 370 move up and down. Washing fluid is supplied to the fluid distribution box 368 via a fluid input line (not illustrated) affixed to fluid distribution box input 372. The washing fluid then flows through the fluid distribution box 368 to the manifold dispensers 340, and out of the manifold dispensers to wash the laboratory consumables.

Referring now to FIGS. 20 and 21, the pipette tip washing device 310 may comprise a splashguard 430 that at least partially surrounds and projects downward from the manifold dispenser 400 (or any other suitable manifold dispenser). Such a splashguard helps keep more of the washing fluid directed at the laboratory consumables being washed. The splashguard 430 moves up and down in conjunction with the manifold dispenser 400. The splashguard 430 at least partially surrounds a top edge of the rack holding the laboratory consumables when the manifold dispenser is in its washing position. The splashguard 430 comprises a plurality of side walls 432 projecting downward from a top wall 436. One or more of the side walls 432 may have a flange 434 that projects further downward. An opening 438 is defined on one side for receiving the manifold dispenser 400. When the splashguard 430 is used, a different top surface or platform may be needed to accommodate the flanges 434 of the splashguard 430. As seen in FIG. 21, top surface or platform 440 (which defines only one opening, but may define any number of openings (including four openings such as top surface 384)) has opposing slots 442 and opposing cutouts 444 for receiving the flanges 434 of the splashguard 430. While the top surface 440 uses a combination of slots and cutouts, just slots or just cutouts may be used.

Referring now to FIG. 22, the top compartment 314 includes a UV curtain 420 that is positioned to project UV light down onto the tops of the laboratory consumables as the drawer compartment 320 is opened and/or closed. In this regard, all of the laboratory consumables are effectively exposed to the UV light, without having to have an undesirably large UV light source. As seen in FIGS. 12, 13 and 17, the UV curtain 420 is affixed to the vertical sides of the inner wall 332 of the top compartment, near the front edge. As seen in FIG. 22, the UV curtain 420 comprises a frame 422, mounting brackets 426 on opposing ends of the frame 422, and one or more UV light bulbs 424. Alternatively to affixing the UV curtain to the vertical sides of the inner wall 332 of the top compartment, the UV curtain may be affixed to the horizontal center section of the inner wall 332, to the front manifold support beam, or to the braces that affix the manifold dispensers to the cylinders of the front manifold support beam (or to any other suitable structure). In another alternative embodiment of the invention (not illustrated), a UV curtain may be movable relative to the laboratory consumables. Such a movable UV curtain may be, for example, mounted on linear tracks on opposing vertical sides of the inner wall 332 and able to move back and forth along the tracks. In such an embodiment, the movable UV curtain may move front to rear and/or rear to front to expose the laboratory consumables to UV light. As another example, such a movable UV curtain may be mounted on linear tracks on front and rear sides (not illustrated) of the inner wall 332 and able to move back and forth along the tracks. In such an embodiment, the movable UV curtain may move left to right and/or right to left to expose the laboratory consumables to UV light. Such a movable UV curtain may move and expose the laboratory consumables to UV light after the drawer compartment is closed but before the manifold dispensers are extended and the wash cycle begins and/or after the wash cycle is complete and the manifold dispensers retracted but before the drawer compartment is opened.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

The invention claimed is:
1. A washing device comprising:
an outer shell in which a top compartment and a middle compartment are positioned, the middle compartment is positioned beneath the top compartment,
the top compartment comprises an inner wall providing support and mounting surfaces for a manifold dispenser, the manifold dispenser comprises at least one liquid input and a plurality of liquid outputs that operably direct fluid to contact a plurality of laboratory consumables held by a rack in the washing device, a number of the plurality of liquid outputs being such that each liquid output of the plurality of liquid outputs operably directs the fluid at a corresponding laboratory consumable of the plurality of laboratory consumables, and the manifold dispenser is capable of being raised and lowered vertically relative to the rack to alternate between loading or unloading, and washing, positions for the plurality of laboratory consumables, the middle compartment comprises an inner wall providing support and mounting surfaces, the middle compartment also comprises a washing chamber receiving and retaining fluid output by the plurality of liquid outputs of the manifold dispensers, the washing chamber is positioned within the inner wall of the middle compartment, and the middle compartment also comprises a compartment positioned within the inner wall of the middle compartment, the compartment being moveable between a loading/unloading position and the washing position, the compartment includes a top surface with openings for receiving racks holding the plurality of laboratory consumables.

2. The washing device of claim 1, wherein the rack comprises a tip rack and the plurality of laboratory consumables comprise a plurality of pipette tips.

3. The washing device of claim 2, wherein the tip rack is configured to hold 24, 48, 96, 384, or 1536 pipette tips.

4. The washing device of claim 1, further comprising at least one transducer capable of outputting sound in an ultrasonic range in at least the second compartment.

5. The washing device of claim 1, further comprising at least one mechanical cylinder that operably agitates the rack.

* * * * *